(12) United States Patent
Kostamovaara et al.

(10) Patent No.: US 10,371,641 B2
(45) Date of Patent: Aug. 6, 2019

(54) METHOD AND APPARATUS FOR MEASURING INELASTIC SCATTERING

(71) Applicant: TimeGate Instruments Oy, Oulu (FI)

(72) Inventors: Juha Kostamovaara, Oulu (FI); Ilkka Nissinen, Oulu (FI); Jan Nissinen, Oulu (FI); Rami Aikio, Vtt (FI); Jussi Tenhunen, Vtt (FI); Lauri Kurki, Vtt (FI)

(73) Assignee: TimeGate Instruments Oy, Oulu (FI)

( * ) Notice: Subject to any disclaimer, the term of this patent is extended or adjusted under 35 U.S.C. 154(b) by 0 days.

(21) Appl. No.: 15/410,867

(22) Filed: Jan. 20, 2017

(65) Prior Publication Data
US 2017/0234797 A1      Aug. 17, 2017

(30) Foreign Application Priority Data

Jan. 21, 2016   (FI) ..................................... 20165037

(51) Int. Cl.
*G01J 3/44*     (2006.01)
*G01N 21/65*    (2006.01)
*G01J 1/44*     (2006.01)

(52) U.S. Cl.
CPC ............... *G01N 21/65* (2013.01); *G01J 3/44* (2013.01); *G01J 2001/442* (2013.01)

(58) Field of Classification Search
CPC ...................................................... G01N 21/65
(Continued)

(56) References Cited

U.S. PATENT DOCUMENTS 6,244,753 B1 *   6/2001  O'Connor ................ G01J 3/44
                                                     385/12
2013/0327129 A1* 12/2013 Jung ...................... G01N 30/74
                                                    73/61.55
(Continued)

FOREIGN PATENT DOCUMENTS

WO       9841846 A1    9/1998
WO    2013027034 A1    2/2013
WO    2014125171 A1    8/2014

OTHER PUBLICATIONS

De Grooth et al., "Gated Raman spectroscopy (GRAS): A new experimental approach for the measurement of Raman signals of particles in suspension.", Review of Scientific Instruments, 1984, vol. 55, No. 2, 3 pages.

*Primary Examiner* — Sunghee Y Gray
(74) *Attorney, Agent, or Firm* — Ziegler IP Law Group, LLC

(57) ABSTRACT

An apparatus, includes an illuminating light source and illuminating optics arranged to illuminate a sample region with illuminating light pulses, light gathering optics to gather Raman scattered light pulses from the sample region, a spectral disperser and a detector array for measuring the spectral intensity distribution of Raman scattered light pulses obtained from the sample region and an auxiliary detector for providing an indicator signal indicative of elastic scattering coefficient of the sample region. The apparatus is arranged to form a first output spectrum from the spectral intensity distribution of a first group of Raman scattered light pulses. The pulses of the first group of Raman scattered light pulses are obtained from the sample region when the indicator signal indicates that an object is located in the sample region.

14 Claims, 11 Drawing Sheets

(58) Field of Classification Search
USPC .......................................................... 356/301
See application file for complete search history.

(56) References Cited

U.S. PATENT DOCUMENTS

| | | |
|---|---|---|
| 2013/0342835 A1 | 12/2013 | Blacksberg |
| 2014/0004559 A1 | 1/2014 | Hill et al. |
| 2016/0116414 A1* | 4/2016 | Day .................. B01D 53/1425 356/36 |
| 2017/0160201 A1* | 6/2017 | Nishizawa ............. G01N 21/65 |
| 2018/0292324 A1* | 10/2018 | Verma .................... G01N 21/65 |

* cited by examiner

METHOD AND APPARATUS FOR MEASURING INELASTIC SCATTERING

FIELD

The aspects of the disclosed embodiments relate to a method and an apparatus for measuring a Raman spectrum.

BACKGROUND

Raman spectroscopy may be used in the chemical analysis of samples. In case of a heterogeneous substance, a conventional Raman measurement may provide a signal, which contains a contribution of a first component of the heterogeneous substance, and a contribution of a second component of the heterogeneous substance. The measured signal may be a temporal average which represents the two (or more) contributing components.

SUMMARY

Some versions may provide a method for measuring Raman spectrum of moving particles of a heterogeneous substance. Some versions may provide an apparatus for measuring Raman spectrum of moving particles of a heterogeneous substance.

According to an aspect, there is provided a method for measuring Raman scattering, the method comprising:
varying composition in a sample region (REG1),
providing an indicator signal (S2) indicative of elastic scattering coefficient of the sample region (REG1),
illuminating the sample region (REG1) with illuminating light pulses (LB0), and
forming a first output spectrum (F1($\lambda$)) from the spectral intensity distribution (I($\lambda$)) of a first group of Raman scattered light pulses (LB1$_R$), wherein the pulses of said first group of Raman scattered light pulses (LB1$_R$) are obtained from the sample region (REG1) when the indicator signal (S2(t)) indicates that an object (O1) is located in the sample region (REG1).

According to an aspect, there is provided an apparatus (500), comprising:
an illuminating light source (LS1) and illuminating optics (10) arranged to illuminate a sample region (REG1) with illuminating light pulses (LB0),
light gathering optics (20) to gather Raman scattered light pulses (LB1$_R$) from the sample region (REG1),
a spectral disperser (200) and a detector array (100) for measuring the spectral intensity distribution (I($\lambda$)) of Raman scattered light pulses (LB1$_R$) obtained from the sample region (REG1),
an auxiliary detector (DET2) for providing an indicator signal (S2) indicative of elastic scattering coefficient of the sample region (REG1),
wherein said apparatus (500) is arranged to form a first output spectrum (F1($\lambda$)) from the spectral intensity distribution (I($\lambda$)) of a first group of Raman scattered light pulses (LB1$_R$), wherein the pulses of said first group of Raman scattered light pulses (LB1$_R$) are obtained from the sample region (REG1) when the indicator signal (S2(t)) indicates that an object (O1) is located in the sample region (REG1).

The method for measuring Raman scattering may comprise:
varying composition in a sample region (REG1),
providing an indicator signal (S2) indicative of elastic scattering coefficient of the sample region (REG1),
illuminating the sample region (REG1) with illuminating light pulses (LB0), and
forming a first output spectrum (F1($\lambda$)) from the spectral intensity distribution (I($\lambda$)) of a first group of Raman scattered light pulses (LB1$_R$), wherein the pulses of said first group of Raman scattered light pulses (LB1$_R$) are obtained from the sample region (REG1) when the indicator signal (S2(t)) indicates that an object (O1) is located in the sample region (REG1).

The method may comprise controlling timing of the illuminating light pulses LB0 based on the indicator signal S2(t) and/or the method may comprise forming an output spectrum by classifying the Raman scattered light pulses LB1$_R$ according to the indicator signal S2(t).

The method may comprise:
varying composition at a sample region,
providing an indicator signal indicative of elastic scattering coefficient of the sample region,
illuminating the sample region with illuminating light pulses,
controlling timing of illuminating light pulses based on the indicator signal, and
forming one or more output signal values by measuring the spectral intensity distribution of Raman scattered light pulses excited by the illuminating light pulses in the sample region.

The method may comprise:
varying composition at a sample region,
providing an indicator signal indicative of elastic scattering coefficient of the sample region,
illuminating the sample region with illuminating light pulses,
obtaining Raman signal values by measuring the spectral intensity distribution of Raman scattered light pulses excited by the illuminating light pulses in the sample region, and
forming one or more output signal values by classifying the Raman signal values according to the indicator signal.

The method and the apparatus may be used e.g. in the chemical analysis of a heterogeneous substance. The heterogeneous substance may contain a plurality of small objects, e.g. cells obtained from a cell culture. The objects may move e.g. due to stirring of the substance. The size of the objects may be e.g. in the range of 10 µm to 100 µm. The objects may move e.g. at a velocity, which is in the range of 0.1 m/s-10 m/s. The contribution of suspending medium may be substantially reduced e.g. by using temporal resolution, which is e.g. shorter than or equal to 1 µs.

The contribution of the suspending medium may be substantially reduced when the Raman-scattered radiation is collected from a small sample region and when the measurement is based on monitoring the presence of an object in the sample region. The sample region may also be called e.g. as a sample volume or as a region of interest (ROI).

The detection limit of Raman spectroscopy may be limited e.g. by shot noise, by the disturbing effect of fluorescence, and/or by the dark current of the detector. The detector of the measuring apparatus may comprise e.g. an array of single photon avalanche diodes (SPAD) for measuring the intensity of the Raman scattered radiation. The detector array of the apparatus may be arranged to measure the intensity of the Raman scattered radiation by using time gated detection where the integration time of the detector may be set with a temporal resolution which is e.g. shorter than or equal to 100 ps. The illuminating light pulses used for the excitation of the Raman scattered radiation may be obtained e.g. from a solid state laser. The repetition rate of the laser may be e.g. in the range of 10 kHz to 1000 kHz.

The method and the apparatus may allow measuring the Raman spectrum of objects of the heterogeneous substance such that the contribution of the suspending medium is reduced or eliminated. This may allow e.g. performing chemical analysis of the objects of the heterogeneous substance with an improved accuracy. This may allow e.g. more accurate compensation of an error caused by fluorescence of the objects on the Raman spectrum of the objects.

The method and the apparatus may allow obtaining Raman spectroscopic data from a heterogeneous sample. The method and the apparatus may allow attaining a low detection limit for a Raman measurement from the heterogeneous sample. The method and the apparatus may allow obtaining Raman spectroscopic data from a dilute heterogeneous sample.

The method and the apparatus may allow obtaining Raman spectroscopic data from a heterogeneous sample during an early stage of cell growth process where the concentration (volume fraction) of the cells is low.

The method may comprise detecting the presence of a cell or another particle in the region of interest of the apparatus, and classifying the emission (Raman) spectra corresponding to each excitation pulse.

The method may comprise monitoring the presence of an object in the sample region, measuring a Raman spectrum of material located in the sample region, and classifying the measured Raman spectrum to be an object-related spectrum if an object is present in the sample region during measuring said Raman spectrum. The measured Raman spectrum may be classified to be a medium-related if no object was present in the sample region during measuring said Raman spectrum.

The presence of an object in the sample region may be monitored e.g. by focusing light of an auxiliary continuous wave (CW) laser to the sample region, and by using an auxiliary detector to monitor the intensity of elastically scattered light from the sample region. The elastically scattered light may include Rayleigh-scattered light obtained from a homogeneous medium and/or Mie-scattered light from a particle. The auxiliary detector may provide an indicator signal, which is indicative of the elastic scattering cross section of the material located in the sample region. The auxiliary detector may be e.g. an avalanche photodiode (APD). The intensity of elastically scattered light obtained from a particle may be higher than the intensity of elastically scattered light obtained from the suspending medium. When the indicator signal exceeds a predetermined threshold limit, this may be interpreted to be an indication that an object is present in the sample region. When the indicator signal remains below said predetermined threshold limit (or below a second limit), this may be interpreted to be an indication that no object is present in the sample region. Consequently, a measured Raman spectrum may be classified based on the indicator signal. A measured Raman spectrum may be determined to be an object-related spectrum based on the indicator signal.

The presence of an object in the sample region may be monitored by using an auxiliary detector to monitor the intensity of elastically scattered light obtained when the sample region is illuminated with light pulses. Also in this case, when the indicator signal exceeds a predetermined threshold limit, this may be interpreted to be an indication that an object is present in the sample region.

The method may comprise forming a first output result from spectra which are classified to be object-related. The method may comprise forming a second output result from spectra which are classified to be medium-related (i.e. not object-related). The method may comprise forming the first output result and forming the second output result.

The method may comprise forming the first output result or forming the second output result exclusively, i.e. the method may comprise forming the first output result without forming the second output result, or the method may comprise forming the second output result without forming the first output result.

One way to realize the exclusive classification is to enable the array detector only when the indicator signal indicates that an object is present in the sample region.

The first output result and the second output result may be formed e.g. by storing the single-pulse spectra to different memory banks according to the indicator signal. These memory banks may be implemented e.g. on the chip of a detector array, or outside said chip.

The method and the apparatus may provide e.g. information about an industrial system, which contains a flow of heterogeneous substance. The heterogeneous substance may comprise e.g. aerosol particles or cells obtained from cell culture.

The Raman spectrum may be measured e.g. by using an array of single photon avalanche diodes (SPAD). The detector array may be enabled and disabled based on timing of the illuminating light pulses, so as to reduce signal noise.

The Raman spectrum may be measured e.g. by using an electron multiplying charge coupled device (EMCCD). The EMCCD detector may also be enabled and disabled based on timing of the illuminating light pulses, so as to reduce signal noise.

BRIEF DESCRIPTION OF THE DRAWINGS

In the following examples, several variations will be described in more detail with reference to the appended drawings, in which.

DETAILED DESCRIPTION

Figure 1A:
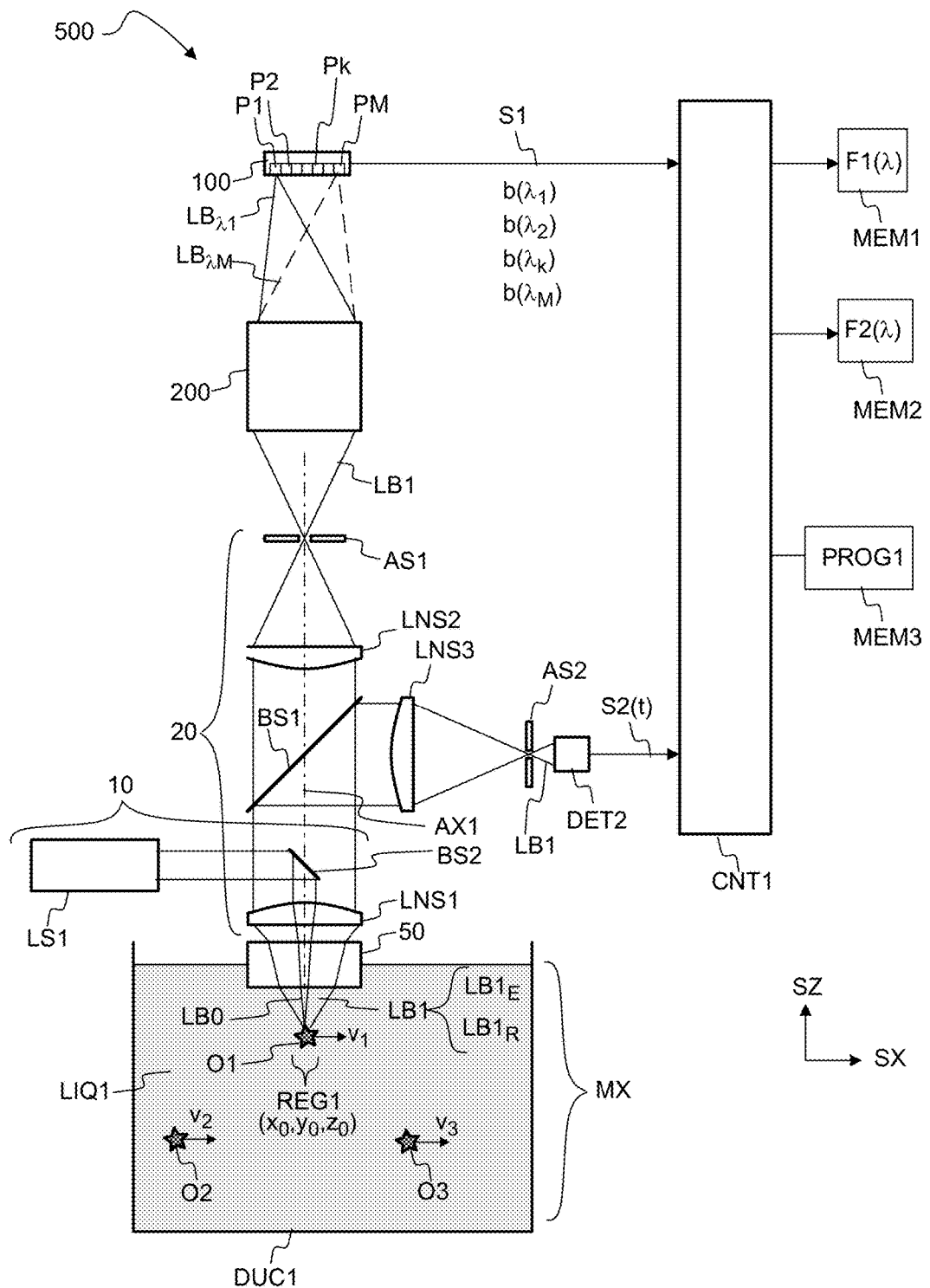
FIG. 1a shows, by way of example, an apparatus arranged to measure the Raman spectrum of objects suspended in a medium.

Referring to FIG. 1a, the measuring apparatus 500 may comprise a light source LS1, which may be arranged to provide illuminating light pulses LB0 (i.e. pulsed illuminating light LB0). The measuring apparatus 500 may be arranged to illuminate a sample region REG1 with the light pulses LB0. The sample region may also be called e.g. as a sample volume or as a region of interest (ROI).

The apparatus 500 may comprise e.g. a pulsed laser LS1 to provide illuminating light pulses LB0. The laser LS1 may be e.g. a Nd:YAG laser operating at the wavelength of 1064 nm, 532 nm, or 355 nm. The laser may comprise e.g. a nonlinear crystal to provide laser pulses by second harmonic generation or by triple harmonic generation. The light source LS1 may be a laser, which has a tuneable output wavelength. The laser LS1 may be e.g. an passively Q-switched laser. The laser LS1 may be e.g. an actively Q-switched laser to allow triggering of illuminating light pulses LB0 according to an indicator signal $S2(t)$. The laser LS1 may be e.g. an excimer laser. The laser LS1 may be e.g. a solid state diode laser. The light source LS1 may be e.g. a fiber laser. The light source LS1 may e.g. a microchip laser. The light source LS1 may comprise e.g. an optical amplifier, which comprises light-amplifying optical fiber. The light source LS1 may comprise e.g. an optical amplifier, which comprises light-amplifying optical bulk crystal. The illuminating light pulses LB0 may be laser pulses.

The light source LS1 may also be a continuous wave laser. The operation of the continuous wave laser may switched on and off based on the indicator signal $S2(t)$, e.g. when the velocity $v_1$ of the objects O1 is low. The light source LS1 may also be a continuous wave laser where the output is controlled e.g. by a shutter or an optical modulator based on the indicator signal $S2(t)$.

The measuring apparatus 500 may be arranged to focus the light pulses LB0 to a heterogeneous substance MX. The heterogeneous substance MX may comprise a plurality of objects O1, O2, O3 suspended in a carrier medium LIQ1.

The composition of material located in the sample region REG1 may vary. Movement of the heterogeneous substance MX with respect to the apparatus 500 may cause a change of composition in the sample region REG1. Movement of the objects with respect to the apparatus 500 may cause a change of composition in the sample region REG1. The composition may be varied by moving the heterogeneous substance MX with respect to the sample region REG1.

The carrier medium LIQ1 may be e.g. a liquid or a liquid solution. The carrier medium LIQ1 may be e.g. water or an aqueous solution. The objects O1, O2, O3 may be e.g. (biological) cells suspended in a liquid LIQ1. The objects O1, O2, O3 may be e.g. particles suspended in a liquid LIQ1. The objects O1, O2, O3 may be e.g. aerosol particles suspended in a gas. The objects O1, O2, O3 may be moving with respect to the sample region REG1. The object O1 may move e.g. at a velocity v1, the object O2 may move e.g. at a velocity v2, and the object O3 may move e.g. at a velocity v3 with respect to the sample region REG1. The movement of the objects may be caused e.g. by stirring, pumping and/or convection of the substance MX. The movement of an object O1 may also be caused e.g. by buoyancy, or settling. The medium LIQ1 may move such that the objects O1, O2, O3 move with respect to the sample region REG1. The center of the sample region REG1 may be at a position specified by coordinates $(x_0, y_0, z_0)$. The heterogeneous substance MX may be contained e.g. in a container DUC1, and/or the heterogeneous substance MX may be moving in a flow duct DUC1. The container DUC1 may be e.g. a test tube, or a reaction vessel. The duct DUC1 may be connected to a reaction vessel.

The light pulses LB0 may be brought into the heterogeneous substance MX e.g. through a window 50. The window 50 may be in contact with the substance MX. The window 50 may be e.g. a part of the apparatus 500 or a part of a process vessel. In an embodiment, a lens LNS1 of the apparatus 500 may be arranged to operate as the window 50.

The light pulses LB0 may be brought into the heterogeneous substance MX also without using a window 50. For example, the light pulses LB0 may be brought into the heterogeneous substance MX through a gas-liquid interface between air and the heterogeneous substance MX.

The light pulses LB0 may be focused to the sample region REG1 e.g. by focusing optics. The focusing optics may comprise e.g. one or more lenses (e.g. the lens LNS1). The light LB0 may be focused to the sample region REG1 e.g. as a converging light beam such that said beam has a waist (i.e. the narrowest part) at the sample region REG1. The apparatus 500 may comprise illuminating optics 10, which may comprise e.g. the light source LS1 and at least one focusing lens LNS1.

Material located in the sample region REG1 may provide scattered light LB1 when illuminated by an illuminating light pulse LB0. The light LB1 may include Raman scattered light $LB1_R$ and/or elastically scattered light $LB1_E$. The elastically scattered light $LB1_E$ may include Rayleigh-scattered light from a homogeneous substance LIQ1. The elastically scattered light $LB1_E$ may include Mie-scattered light from a particle O1. The elastically scattered light $LB1_E$ may include Rayleigh-scattered light from the medium LIQ1 and/or Mie-scattered light from the object O1. The material may provide elastically scattered light $LB1_E$ when illuminated by an illuminating light pulse LB0, and the material may provide Raman scattered light $LB1_R$ when illuminated by the illuminating light pulse LB0.

The measuring apparatus 500 may comprise light gathering optics 20 to collect the light LB1 from the sample region REG1 to a spectrometer. The light gathering optics 20 may also define the spatial position of the sample region REG1. The light gathering optics 20 may also comprise e.g. an aperture stop AS1 for defining the spatial position of the sample region REG1.

The spectrometer may comprise a spectral disperser 200 and a detector 100. The disperser 200 may decompose the gathered light LB1 e.g. into spectral components $LB_{\lambda 1}$, $LB_{\lambda 2}$, $LB_{\lambda k}$, $LB_{\lambda M}$, and the disperser 200 may direct the spectral components $LB_{\lambda 1}$, $LB_{\lambda 2}$, $LB_{\lambda k}$, $LB_{\lambda M}$ to different spatial positions of the detector 100. The disperser 200 may comprise e.g. one or more diffraction gratings and/or prisms. The detector 100 may comprise an array of detector pixels P1, P2, Pk, PM. Each detector pixel P1, P2, Pk, PM of the detector 100 may be arranged to measure the intensity of light LB1 at a different wavelength $\lambda_1$, $\lambda_2$, $\lambda_k$, $\lambda_M$. For example, the component $LB_{\lambda 1}$ may be directed to the detector pixel P1, the component $LB_{\lambda 2}$ may be directed to the detector pixel P2, the component $LB_{\lambda k}$ may be directed to the detector pixel Pk, and the component $LB_{\lambda M}$ may be directed to the detector pixel PM. Each detector pixel P1, P2, Pk, PM of the detector 100 may be arranged to measure the intensity of light LB1 at a different wavelength band, wherein the wavelengths $\lambda_1$, $\lambda_2$, $\lambda_k$, $\lambda_M$ may denote the centers of said wavelength bands, respectively. M may denote the number of the different wavelength bands.

The detector 100 may comprise e.g. an array of single photon avalanche diodes (SPAD). The method may comprise measuring the spectral intensity distribution ($I(\lambda)$) of Raman scattered light pulses ($LB1_R$) by using an array (100) of single photon avalanche photodiodes (SPAD). Using the SPAD detector may allow reducing the noise level of the measured results.

The detector 100 may be e.g. an electron multiplying charge coupled device (EMCCD). The method may comprise measuring the spectral intensity distribution ($I(\lambda)$) of Raman scattered light pulses ($LB1_R$) by using electron multiplying charge coupled device (EMCCD). The integration of the optical signal with EMCCD may be enabled and disabled with a short time response resulting in no penalty from detector read noise which may be the case when using a CCD detector. Using the EMCCD may thus allow splitting a total measurement time period into a plurality of integration times. Measured data obtained during said integration times may be sorted into separate groups (e.g. in different memory areas) based on the indicator signal S2. Consequently, data related to the objects O1 may be separated from data related to the medium LIQ1 substantially without penalty from detector read noise. The data of a first group may be stored e.g. in a first memory MEM1, and data of a second group may be stored e.g. in a second memory MEM2.

The volume fraction of the medium LIQ1 may be substantially higher than the (combined) volume fraction of the objects. The medium LIQ1 may be the dominant source of the collected photons. By using the EMCCD detector, the signals related to the objects may be effectively separated from the signals related to the medium LIQ1. By using the EMCCD detector the signal-to-noise ratio may be increased since the shot noise rising from photons of the signal LIQ1 is not affecting the signal rising from the objects O1.

The operation of the detector 100 may be controlled based on the indicator signal ($S2(t)$). The operation of the detector 100 may be enabled and disabled based on the indicator signal ($S2(t)$). The SPAD detector 100 may comprise a set of counters (See FIG. 8c). The operation of said set of counters may be enabled and disabled based on the indicator signal ($S2(t)$).

The detector 100 may provide a detector signal S1. The signal S1 may comprise a plurality of measured Raman signal values $b(\lambda_1)$, $b(\lambda_2)$, $b(\lambda_k)$, $b(\lambda_M)$. Each Raman signal value $b(\lambda_1)$, $b(\lambda_2)$, $b(\lambda_k)$, $b(\lambda_M)$ may indicate the spectral intensity of Raman scattered light at a spectral position $\lambda_1$, $\lambda_2$, $\lambda_k$, $\lambda_M$.

The light gathering optics 20 may comprise e.g. one or more lenses LNS1, LNS2 and an aperture stop AS1. The aperture stop AS1 may define the boundary of the sample region REG1 such that light scattered from material outside the sample region REG1 is not effectively coupled to via the disperser 200 to the detector 100. The focusing optics of the apparatus 500 may be arranged to operate such that the intensity of illuminating light LB0 outside the sample region REG1 is substantially lower than the intensity of illuminating light LB0 inside the sample region REG1.

The apparatus 500 may optionally comprise an optical fiber for guiding the light LB1 from the aperture stop AS1 to the disperser 200. An end of the optical fiber may be arranged to operate as the aperture stop AS1. The apparatus 500 may optionally comprise an optical fiber for guiding the illuminating light pulses LB0 from the light source LS1 to the focusing optics.

The apparatus 500 may comprise an auxiliary detector DET2, which may be arranged to monitor when an object is present in the sample region REG1. The auxiliary detector DET2 may be arranged to monitor when an object at least partly overlaps the sample region REG1. The apparatus 500 may comprise an aperture stop AS2 for defining a detection volume such that light scattered from material inside the detection volume may be guided to the auxiliary detector DET2 and such that that light scattered from material outside the detection volume is not guided to the auxiliary detector DET2. The apparatus 500 may be arranged to operate such that the detection volume of the auxiliary detector DET2 substantially coincides with the sample region REG1. Consequently, the auxiliary detector DET2 may be arranged to monitor whether an object is located in the sample region REG1. The detector DET2 may provide a signal $S2(t)$. The signal $S2(t)$ may be indicative of the presence of an object in the sample region REG1. The signal $S2(t)$ may be called e.g. as an indicator signal. The indicator signal $S2(t)$ may be e.g. substantially proportional to the intensity of elastically scattered light $LB1_E$ impinging on the detector DET2. The indicator signal $S2(t)$ may be indicative of the ratio of the intensity of elastically scattered light $LB1_E$ obtained from the sample volume REG1 to the intensity of illuminating light pulse LB0. The indicator signal $S2(t)$ may be indicative of the elastic scattering cross section of the sample region REG1.

The illumination of the sample region REG1 by the light pulses LB1 and gathering of light LB1 from the sample region REG1 may be arranged to take place by a confocal arrangement. The illuminating optics 10 and the light gathering optics 20 may share at least one common lens LNS1. The optical axis of the illuminating optics 10 may substantially coincide with the optical axis of the light gathering optics 20. The optical axis of the focusing optics of the illuminating optics 10 may substantially coincide with the optical axis of the light gathering optics 20.

The apparatus 500 may comprise a control unit CNT1 for controlling operation of the apparatus 500 and/or for processing the signals S1, $S2(t)$. For example, the control unit CNT1 may be arranged to form one or more output results F1($\lambda$), F2($\lambda$) from Raman signal values b($\lambda_1$), b($\lambda_2$), b($\lambda_k$), b($\lambda_M$) obtained from the detector 100. The control unit CNT1 may be arranged to form a first output spectrum F1($\lambda$) from a first group of Raman signal values b($\lambda_1$), b($\lambda_2$), b($\lambda_k$), b($\lambda_M$) obtained from the detector 100. The control unit CNT1 may be arranged to form a second output spectrum F2($\lambda$) from a second group of Raman signal values b($\lambda_1$), b($\lambda_2$), b($\lambda_k$), b($\lambda_M$) obtained from the detector 100. The apparatus 500 may comprise e.g. a memory MEM1, MEM2, and/or MEM3. The first output result F1($\lambda$) may be stored e.g. in a memory MEM1. The second output result F1($\lambda$) may be stored e.g. in a memory MEM2.

The apparatus 500 may comprise a memory MEM3 for storing computer program PROG1. When executed by one or more data processors CNT1, the computer program PROG1 may cause the apparatus 500 e.g. to measure Raman signal values and/or to process Raman signal values.

The apparatus 500 may comprise e.g. beam splitter BS2 or a mirror for coupling the light pulses LB0 co-axially to the sample region REG1. The light pulses LB0 may be coupled to the sample region REG1 e.g. through a focusing lens LNS1. An illuminating light pulse LB0 may excite scattered light in the material located in the sample region REG1. The scattered light LB1 from the sample region REG1 may be gathered e.g. by a light gathering lens LNS1. The same lens LNS1 may be used for focusing the illuminating light pulses LB0 to the sample region REG1 and for collecting the scattered light LB1.

The apparatus 500 may comprise e.g. a beam splitter BS1 or a mirror for coupling a first part of the scattered light LB1 gathered from the sample region REG1 to disperser 200, and for coupling a second part of the scattered light LB1 to the auxiliary detector DET2. The first part of the scattered light LB1 may be focused e.g. by a lens LNS2 via the aperture stop AS1 to the disperser 200. The second part of the scattered light LB1 may be focused e.g. by a lens LNS3 via the aperture stop AS2 to the detector DET2.

SX and SZ denote orthogonal directions. A third direction (SY) may be perpendicular to the directions SX and SZ. The window 50 may be e.g. substantially parallel with a plane defined by the directions SX and SY.

Figure 1B:
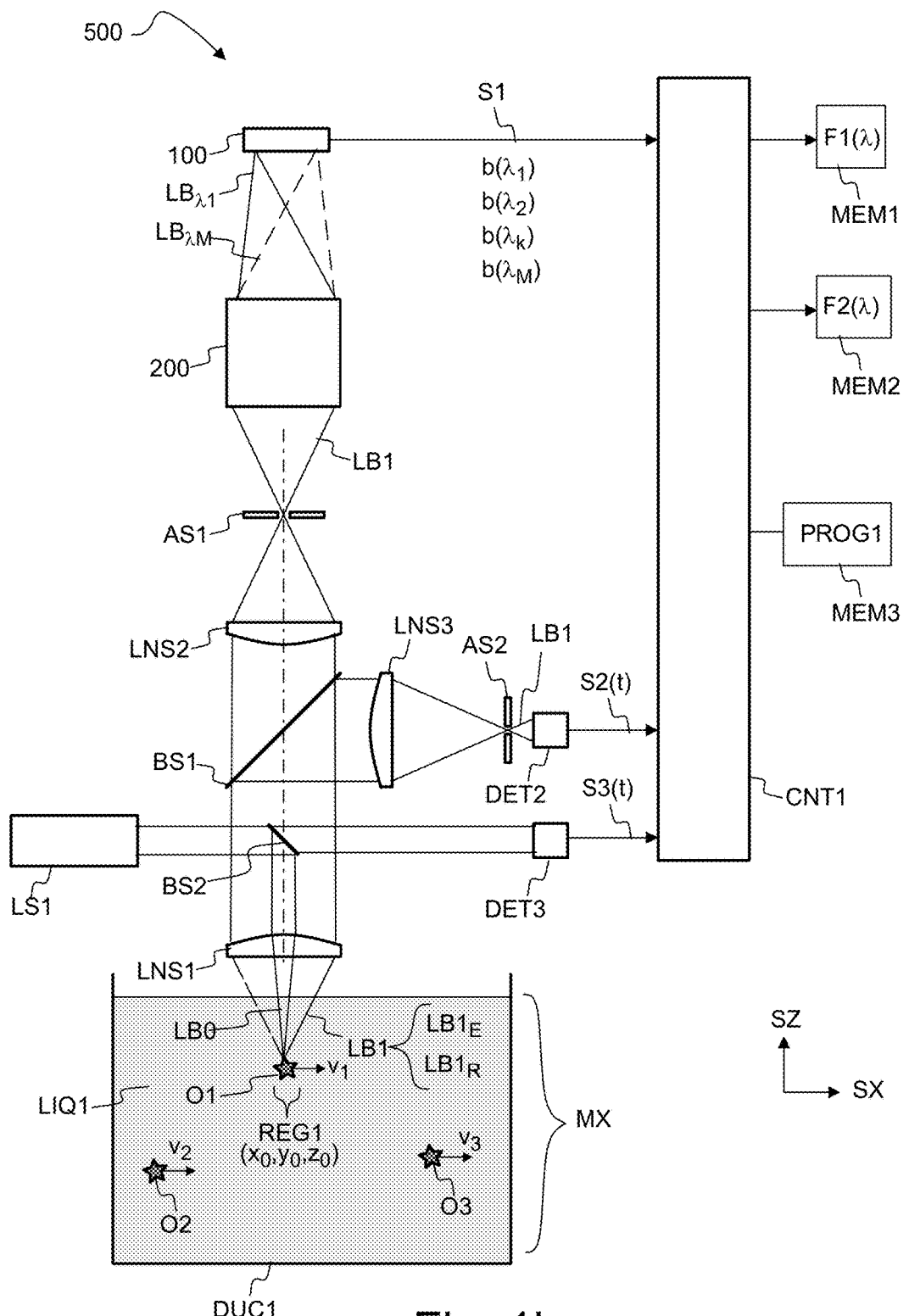
FIG. 1b shows, by way of example, an apparatus arranged to measure the Raman spectrum of objects suspended in a medium.

Referring to FIG. 1b, the apparatus 500 may further comprise a second auxiliary detector DET3 for monitoring the timing of the illuminating light pulses LB0. A part of the light of the illuminating light pulses LB0 may be coupled to the detector DET3 e.g. by a beam splitter BS2 or by a beam splitter BS3 (see FIG. 1c). The detector DET3 may provide a timing signal S3(t) indicative of the timing of the illuminating light pulses LB3. The timing signal S3(t) may comprise a trigger pulse $S_{TRG}$ e.g. for precise timing of operation of the apparatus 500.

Figure 1C:
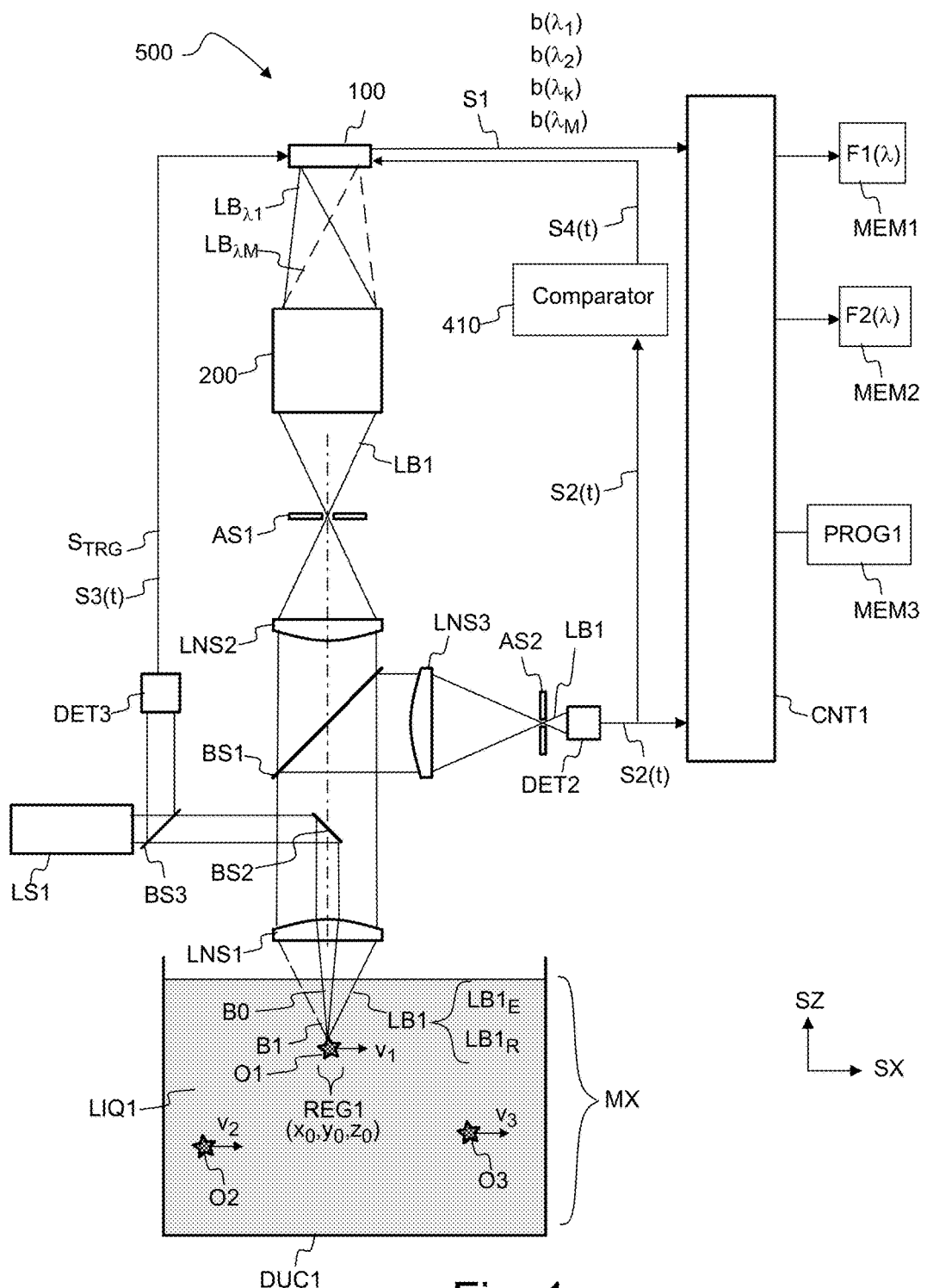
FIG. 1c shows, by way of example, an apparatus arranged to measure the Raman spectrum of objects suspended in a medium.

Referring to FIG. 1c, the timing signal S3(t) may be coupled from the detector DET3 to the detector 100 e.g. in order to reduce timing errors and/or in order to reduce a time delay caused by propagation of the signal S3(t). The detector DET3 may provide a timing signal S3(t) indicative of the timing of the illuminating light pulses LB3. The timing signal S3(t) may comprise a trigger pulse $S_{TRG}$ e.g. for precise timing of operation of detector 100.

The method may comprise controlling operation of the detector 100 based on the indicator signal S2(t). The method may comprise enabling operation of the detector 100 based on the indicator signal S2(t).

The apparatus 500 may comprise e.g. a comparator 410 for determining when the indicator signal S2(t) indicates the presence of an object in the sample region REG1. The comparator 410 may be arranged to provide a control signal S4(t) for enabling operation of the detector 100. The comparator 410 may provide the control signal S4(t) based on the indicator signal S2(t). The comparator 410 may provide the control signal S4(t) e.g. by comparing the indicator signal S2(t) with a reference value LIM1.

The comparator 410 may be implemented e.g. on the detector DET2, on the detector 100, on the control unit CNT1, or as a separate unit.

When using a SPAD detector 100, the detector 100 may comprise a set of counters arranged to count pulses provide by the photodiodes. The operation of said set of counters may be enabled and disabled based on the indicator signal S2(t) (See FIG. 8c).

Figure 2:
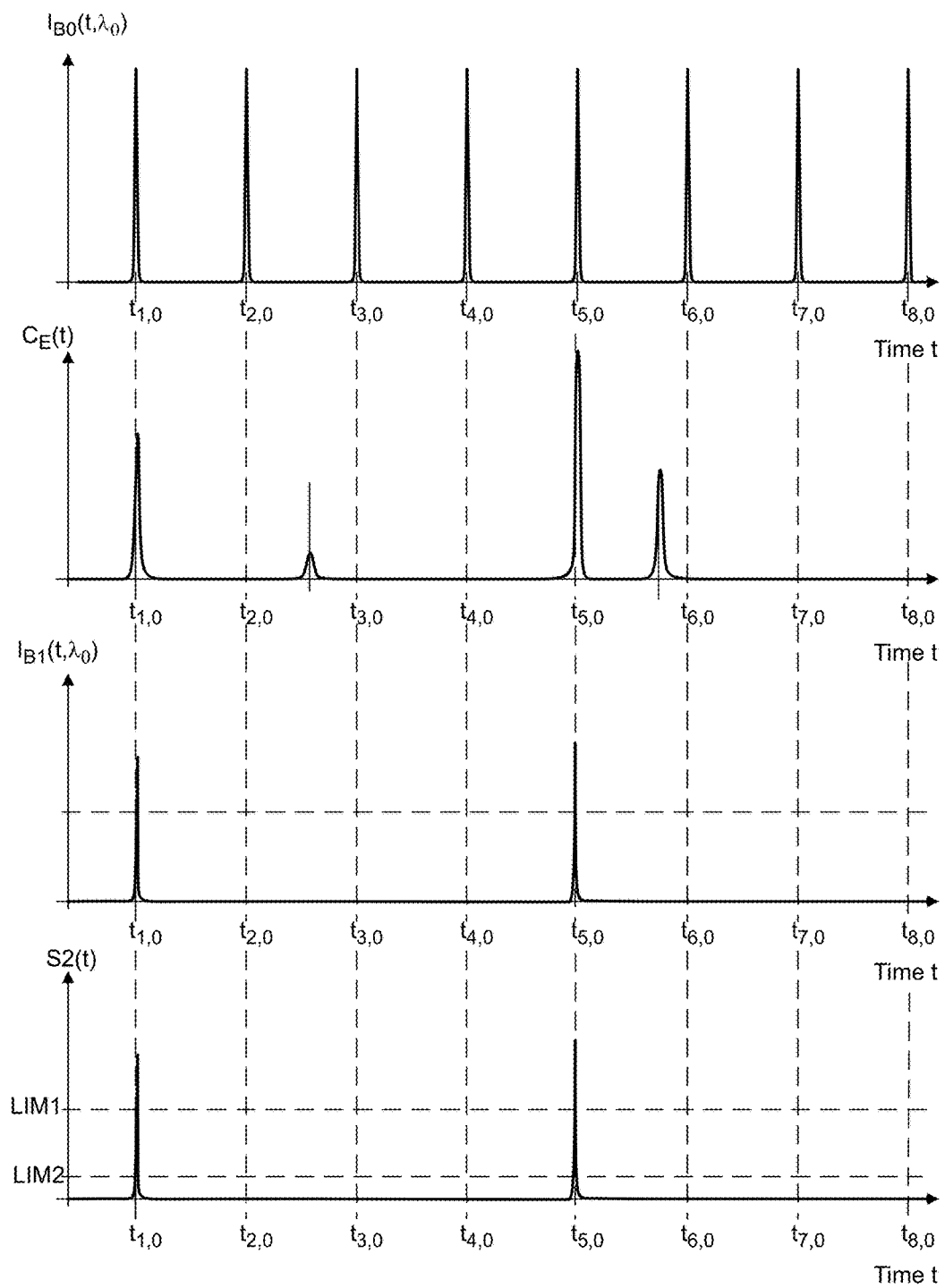
FIG. 2 shows, by way of example, temporal evolution of intensity of illuminating laser pulses, temporal evolution of elastic scattering coefficient, temporal evolution of intensity of light scattered by elastic scattering, and temporal evolution of the indicator signal.

FIG. 2 illustrates operation of the apparatus 500 in a situation where the light source LS1 is arranged to provide illuminating light pulses LB0 such that the time period between consecutive pulses is substantially constant. The light source LS1 may provide the illuminating light pulses LB0 at a (selected) repetition rate. The light source LS1 may provide a pulse LB0 e.g. at times $t_{1,0}$, $t_{2,0}$, $t_{3,0}$, $t_{4,0}$, $t_{5,0}$, $t_{6,0}$, $t_{7,0}$, $t_{8,0}$. $\lambda_0$ denotes the central wavelength of the light pulses LB0. $I_{B0}(t,\lambda_0)$ denotes the spectral intensity of the light pulses LB0 as the function of time t.

The second curve $C_E(t)$ from the top of FIG. 2 shows temporal evolution of the elastic scattering cross section $C_E$ of the sample volume. The elastic scattering cross section $C_E$ may also be called e.g. as the elastic scattering coefficient.

The wavelength of the elastically scattered light is equal to the wavelength $\lambda_0$ of the illuminating light pulses LB0. The intensity $I_{B1}(t,\lambda_0)$ of elastically scattered light detected by the auxiliary detector DET2 may be proportional to the product $C_E(t) \cdot I_{B0}(t,\lambda_0)$. The indicator signal S2(t) provided by the auxiliary detector DET2 may be proportional to the intensity $I_{B1}(t,\lambda_0)$. The indicator signal S2(t) may be indicative of the intensity $I_{B1}(t,\lambda_0)$. The indicator signal S2(t) may be indicative of the elastic cross section $C_E(t)$ of the sample volume REG1.

The apparatus 500 may be configured to detect when the indicator signal S2(t) is higher than or equal to a threshold value LIM1. When the indicator signal S2(t) is higher than or equal to a threshold value LIM1, this may be interpreted to be an indication of the presence of an object in the sample region REG1. When the indicator signal S2(t) is lower than the threshold value LIM1, this may be interpreted to be an indication that an object is not properly present in the sample region REG1.

The method may comprise:
- determining whether a Raman scattered light pulse $LB1_R$ belongs to a first category or not, wherein the Raman scattered light pulse $LB1_R$ is determined to belong to the first category only if the indicator signal S2(t) exceeds a predetermined level LIM1 when the Raman scattered light pulse $LB1_R$ is obtained from the sample region REG1, and
- forming the first output spectrum F1($\lambda$) from the spectral intensity distribution I($\lambda$) of Raman scattered light pulses $LB1_R$ of the first category.

The apparatus 500 may also be configured to detect when the indicator signal S2(t) is lower than a second threshold value LIM2. The second threshold value LIM2 may be lower than said first threshold value LIM2. When the indicator signal S2(t) is lower than the second threshold value LIM2, this may be interpreted to be an indication that no object is overlapping the sample region REG1. When the indicator signal S2(t) is lower than the second threshold value LIM2, this may be interpreted to be an indication that substantially 100% of the Raman-scattered radiation is emitted from the medium LIQ1. When the aim is to analyze the medium LIQ1, an output spectrum $F2(\lambda)$ may be formed (only) from the spectral intensity distribution of the Raman-scattered light pulses LB1 which are obtained when the indicator signal $S2(t)$ is lower than the threshold value LIM2. Consequently, the contribution of the objects O1, O2, O3 to the output spectrum $F2(\lambda)$ may be reduced or eliminated.

The method may comprise:
  determining whether a Raman scattered light pulse $LB1_R$ belongs to a second category or not, wherein the Raman scattered light pulse $LB1_R$ is determined to belong to the second category only if the indicator signal $S2(t)$ is below a predetermined level LIM2 when the Raman scattered light pulse $LB1_R$ is obtained from the sample region REG1, and
  forming a second output spectrum $F2(\lambda)$ from the spectral intensity distribution $I(\lambda)$ of Raman scattered light pulses $LB1_R$ of the second category.

In case of FIG. 2, the elastically scattered light monitored by the detector DET2 is excited by the illuminating light pulses LB0. The indicator signal $S2(t)$ may indicate the presence of an object in the sample region REG1 when a light pulse LB0 temporally coincides with the presence of said object in the sample region REG1. However, one or more objects O1, O2, O3 may also move through the sample region REG1 e.g. at times $t_a$, $t_b$ such that none of the light pulses LB0 temporally coincides with the presence of said object.

Figure 3A:
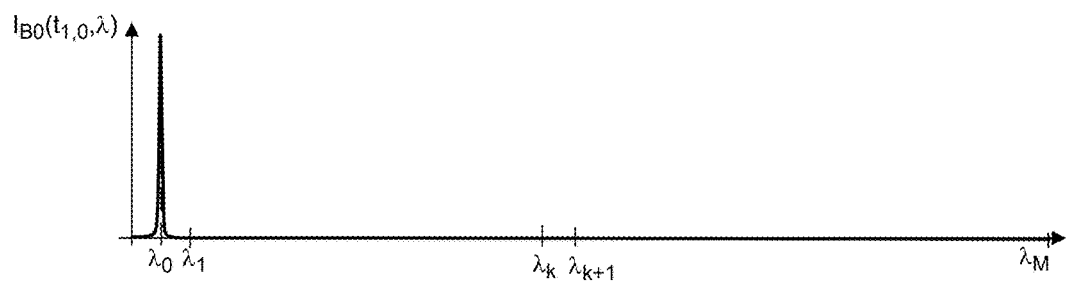
FIG. 3a shows, by way of example, the spectral intensity distribution of an illuminating light pulse.

Referring to FIG. 3a, an illuminating light pulse LB0 generated at a time $t_{1,0}$ has a spectral peak, which is located at the wavelength $\lambda_0$.

Figure 3B:
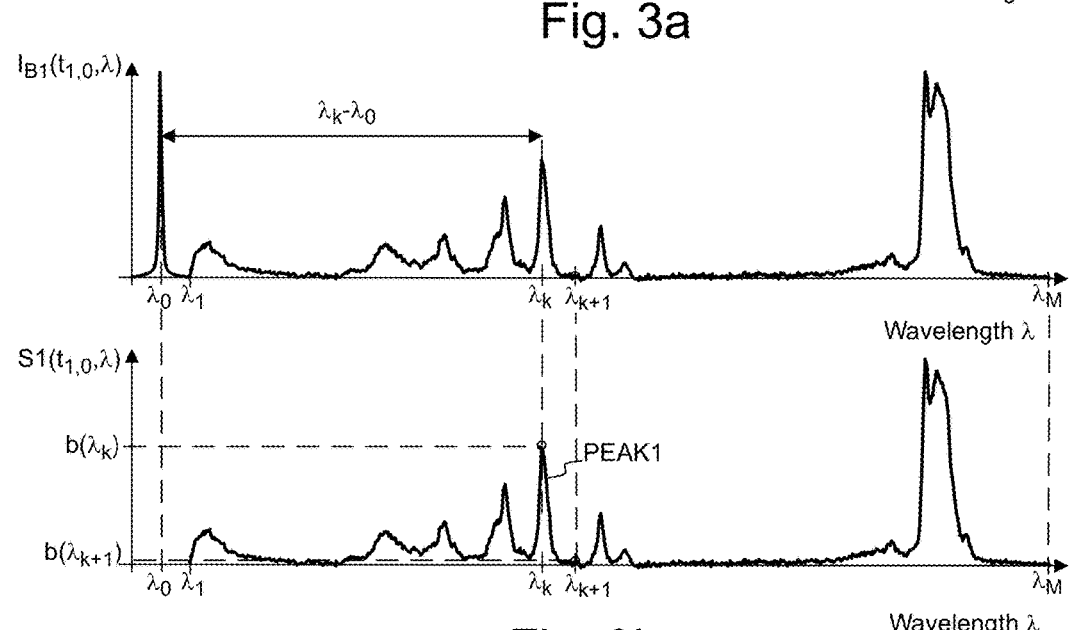
FIG. 3b shows, by way of example, the spectral intensity distribution of the Raman spectrum of an object, and the measured spectral intensity distribution provided by the detector.

FIG. 3b shows, by way of example, the spectral intensity distribution $I_{B1}(\lambda)$ of Raman scattered light obtained from an object O1 at the time $t_{1,0}$. FIG. 3b also shows the measured spectral intensity distribution $S1(\lambda)$ which may be provided by the detector 100 when the detector 100 is arranged to measure said spectral intensity distribution $I_{B1}(\lambda)$. The measured spectrum $S1(\lambda)$ may comprise a plurality of Raman signal values $b(\lambda_1)$, $b(\lambda_k)$, $b(\lambda_{k+1})$, $b(\lambda_M)$. The Raman spectrum of the object O1 may comprise e.g. a spectral peak PEAK1 at the wavelength $\lambda_k$. The Raman spectrum of the object O1 may comprise e.g. a reference point at the wavelength $\lambda_{k+1}$. The height $b(\lambda_{k+1})-b(\lambda_k)$ of the spectral peak PEAK1, when compared with the reference point, may be used e.g. for estimating the chemical composition of the object O1.

Measured Raman signal values $b(\lambda_1)$, $b(\lambda_k)$, $b(\lambda_{k+1})$, $b(\lambda_M)$ obtained from a plurality of different objects O1, O2, O3 may be combined to form an output result $F1(\lambda)$. The method may comprise forming the output result $F1(\lambda)$ from measured Raman signal values $b(\lambda_1)$, $b(\lambda_k)$, $b(\lambda_{k+1})$, $b(\lambda_M)$ obtained from a plurality of different objects O1, O2, O3. The method may comprise forming the output result $F1(\lambda)$ based on the indicator signal $S2(t)$ such that the contribution of the medium LIQ1 to the output result $F1(\lambda)$ is reduced.

The method may comprise forming a first output spectrum $F1(\lambda)$ from the spectral intensity distribution $I(\lambda)$ of a first group of Raman scattered light pulses $LB1_R$. The first group may consist of pulses which are obtained when the indicator signal $S2(t)$ is higher than the threshold value LIM1. The pulses of the first group may belong to a first category.

Figure 3C:
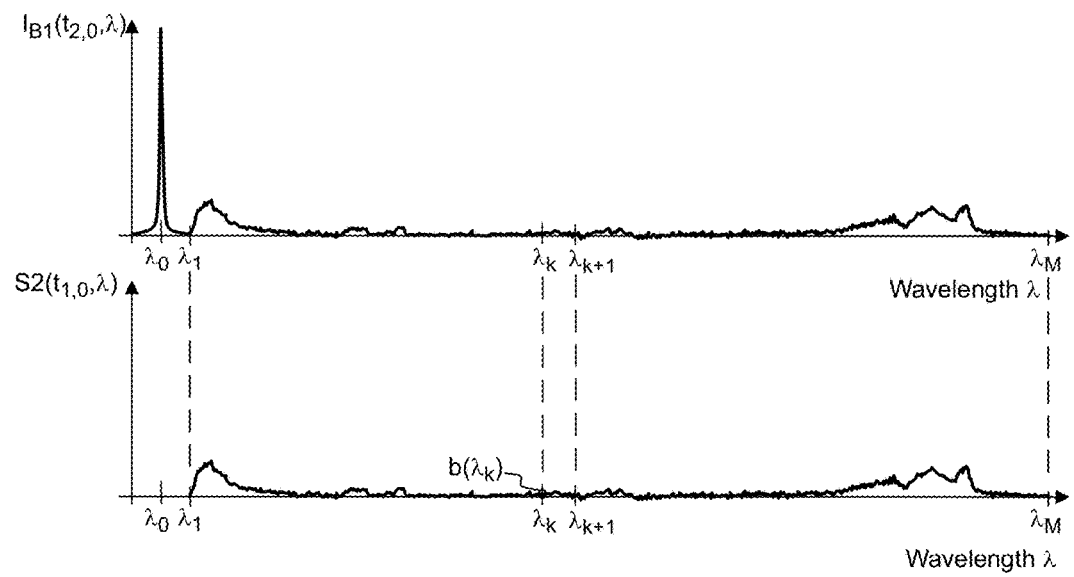
FIG. 3c shows, by way of example, the spectral intensity distribution of the Raman spectrum of the suspending medium, and the measured spectral intensity distribution provided by the detector.

FIG. 3c shows, by way of example, the spectral intensity distribution $I_{B1}(\lambda)$ of Raman scattered light obtained from the medium LIQ1 at the time $t_{2,0}$. FIG. 3b also shows the measured spectral intensity distribution $S1(\lambda)$ which may be provided by the detector 100 when the detector 100 is arranged to measure said spectral intensity distribution $I_{B1}(\lambda)$. The measured spectrum $S1(\lambda)$ may comprise a plurality of Raman signal values $b(\lambda_1)$, $b(\lambda_k)$, $b(\lambda_{k+1})$, $b(\lambda_M)$. The Raman spectrum of the medium LIQ1 may be substantially different from the Raman spectrum of the object(s) O1, O2, O3.

The method may comprise forming a second output spectrum $F2(\lambda)$ from the spectral intensity distribution $I(\lambda)$ of a second group of Raman scattered light pulses $LB1_R$. The second group may consist of pulses $LB1_R$, which are obtained when the indicator signal $S2(t)$ is lower than the threshold value LIM1. The pulses of the first group may belong to a second category.

The method may comprise forming a second output spectrum $F2(\lambda)$ from the spectral intensity distribution $I(\lambda)$ of a second group of Raman scattered light pulses $LB1_R$. The second group may consist of pulses $LB1_R$, which are obtained when the indicator signal $S2(t)$ is lower than the threshold value LIM2 (See FIG. 2).

The method may comprise:
  forming a first output spectrum $F1(\lambda)$ from the spectral intensity distribution $I(\lambda)$ of Raman scattered light pulses $LB1_R$ of the first category, and
  forming a second output spectrum $F2(\lambda)$ from the spectral intensity distribution $I(\lambda)$ of Raman scattered light pulses $LB1_R$ of the second category.

Figure 4:
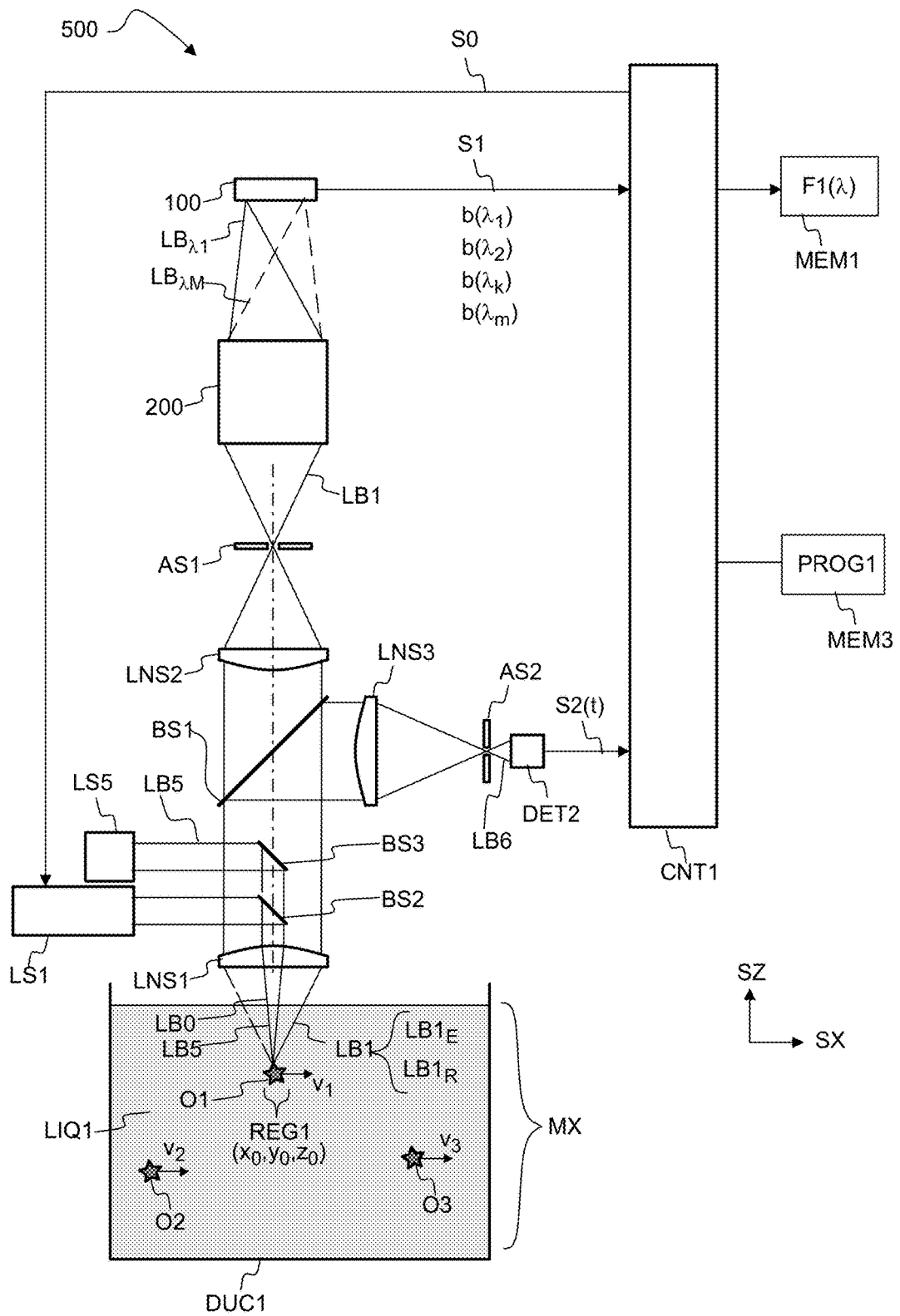
FIG. 4 shows, by way of example, the apparatus arranged to measure the Raman spectrum of objects suspended in a medium, wherein the timing of the illuminating light pulses is controlled based on the indicator signal.

Referring to FIG. 4, the apparatus 500 may comprise an auxiliary light source LS5, which may be arranged to provide auxiliary illuminating light LB5 to the sample region REG1. The auxiliary illuminating light LB5 may be continuous or it may be pulsed at a high repetition rate. The auxiliary illuminating light LB5 may be modulated so as to facilitate reliable detection by the detector DET2.

The wavelength $\lambda_A$ of the auxiliary illuminating light LB5 may e.g. be longer than the longest wavelength of the collected Raman spectrum in order to avoid disturbing measurement of the intensity of the Raman scattered light. The auxiliary illuminating light LB5 may be coupled to the sample region REG1 e.g. by using a beam splitter BS3.

Material located in the sample region REG1 may provide light LB6 by scattering the auxiliary light LB5. The scattered light LB6 may be detected by the auxiliary detector DET2. The auxiliary detector DET2 may provide an indicator signal $S2(t)$ indicative of the presence of an object in the sample region REG1.

The light source LS1 may provide illuminating light pulse LB0 according to a trigger signal S0. The light source LS1 may be e.g. a laser, which is arranged to generate the light pulses LB0 on demand. The apparatus 500 may be arranged to trigger generation of an illuminating light pulse LB0 when indicator signal $S2(t)$ indicates the presence of an object in the sample region REG1.

The method may comprise changing the state of a trigger signal S0 for triggering the illuminating light source LS1 when the indicator signal S2 exceeds a predetermined level LIM1.

The trigger signal S0 may be generated from the indicator signal $S2(t)$ e.g. by determining when the indicator signal $S2(t)$ exceeds a predetermined level LIM1. The trigger signal S0 may be generated e.g. by a comparator. The comparator may be implemented e.g. in the detector DET2, in the control unit CNT1, or as a separate unit.

The detector 100 may be e.g. a SPAD detector or an EMCCD detector in order to provide low signal noise.

The detector 100 may be a charge coupled device (CCD). The apparatus 500 may comprise a CCD detector such that the detector does not comprise an electron multiplier.

When using a CCD detector 100 or an EMCCD detector 100, the sample region REG1 may be illuminated with the light pulses LB0 e.g. only when the indicator signal S2($t$) indicates the presence of an object in the sample region REG1. The light source LS1 may be triggered based on the indicator signal S2($t$). Thus, a single exposure period of the charge coupled device may comprise detecting Raman scattered light LB1 excited by a plurality of light pulses LB0. The length of said single exposure time may be e.g. in the range of 1 s to 500 s.

A measurement time period may also be divided into a plurality of exposure time periods such that the detector is read after each exposure time period. The length of the exposure time periods may be e.g. in the range of 1 ms to 10 s. The sample region REG1 may be illuminated with the light pulses LB0 e.g. only when the indicator signal S2($t$) indicates the presence of an object in the sample region REG1. The light source LS1 may be triggered based on the indicator signal S2($t$). The number of light pulses LB0 occurring during an exposure time period may be e.g. zero, one, or higher than one. Signal data read from the detector at the end of an exposure time period may be discarded if the number of light pulses LB0 occurring during said exposure time period is zero. An output spectrum may be formed from the signal data associated with exposure time periods, where the number of light pulses LB0 occurring during the exposure time period is at least one.

When using the CCD detector 100, the sample region REG1 may be illuminated with the light pulses LB0 e.g. only when the indicator signal S2($t$) indicates the presence of an object in the sample region REG1. The light source LS1 may be triggered based on the indicator signal S2($t$). Thus, an exposure period of the charge coupled device may comprise detecting Raman scattered light LB1 excited by a plurality of light pulses LB0.

Figure 5:
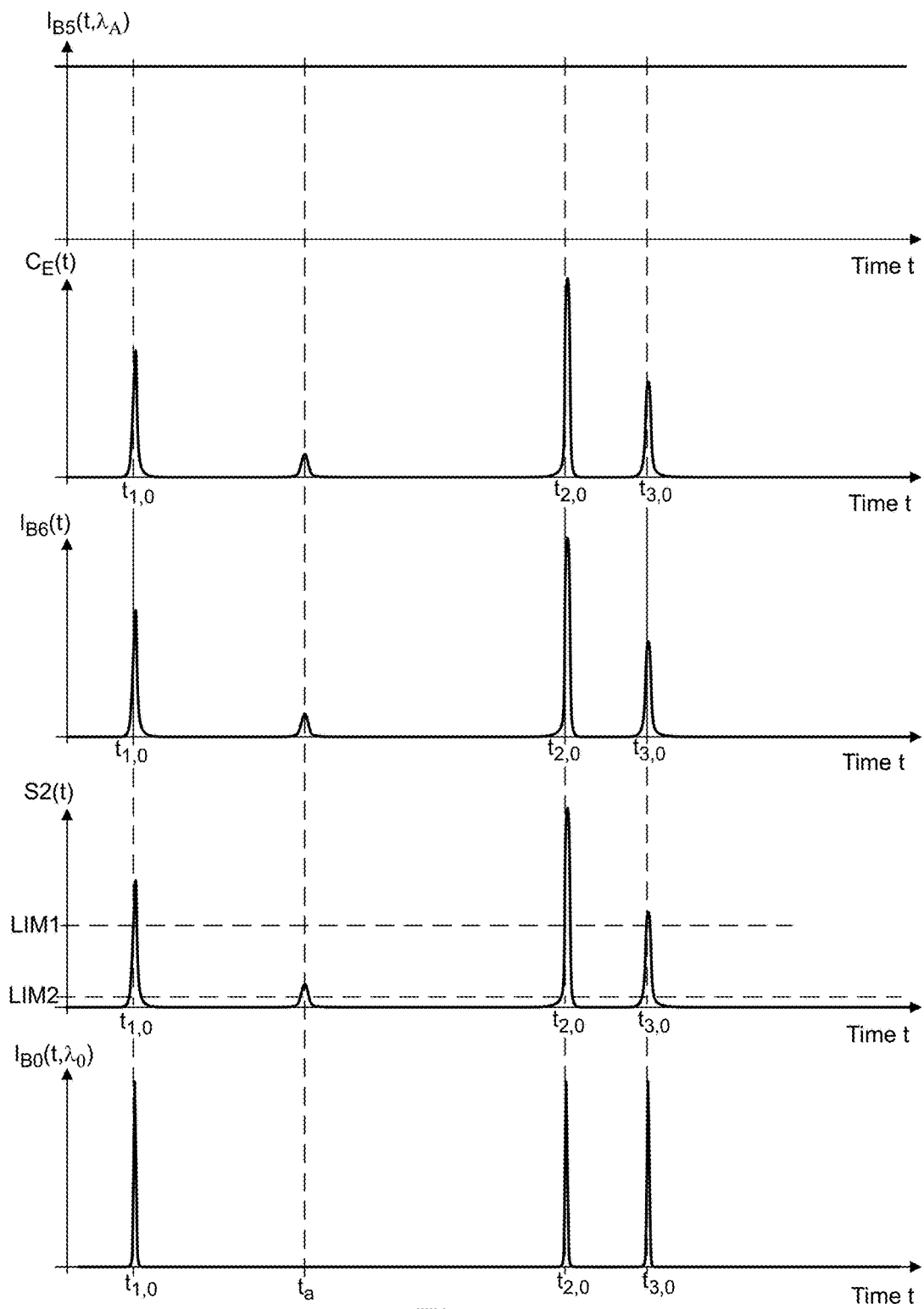
FIG. 5 shows, by way of example, temporal evolution of intensity of auxiliary illuminating light, temporal evolution of elastic scattering coefficient, temporal evolution of intensity of light scattered by elastic scattering, and temporal evolution of intensity of illuminating laser pulses.

FIG. 5 illustrates formation of the indicator signal S2($t$). Referring to the uppermost curve, the auxiliary illuminating light LB5 may illuminate the sample region REG1 continuously or at a high repetition rate. The intensity $I_{B5}(t,\lambda_A)$ of the auxiliary illuminating light LB5 may be substantially constant.

Referring to the second curve from the top, the elastic scattering cross section $C_E(t)$ may vary according to the movements of the objects through the sample region REG1.

Referring to the third curve from the top, the intensity $I_{B6}(t,\lambda_A)$ of the elastically scattered light B6 may be proportional to the product $C_E(t) I_{B5}(t,\lambda_A)$. The indicator signal S2($t$) provided by the auxiliary detector DET2 may be proportional to the intensity $I_{B6}(t,\lambda_A)$. The indicator signal S2($t$) may be indicative of the intensity $I_{B6}(t,\lambda_A)$. The indicator signal S2($t$) may be indicative of the elastic scattering cross section $C_E(t)$ of the sample volume REG1.

The apparatus 500 may be configured to detect when the indicator signal S2($t$) is higher than or equal to a threshold value LIM1. When the indicator signal S2($t$) is higher than or equal to a threshold value LIM1, this may be interpreted to be an indication of the presence of an object in the sample region REG1. When the indicator signal S2($t$) is lower than or equal to the threshold value LIM1, this may be interpreted to be an indication that an object is not properly present in the sample region REG1.

The apparatus 500 may be arranged to operate such that the illuminating light pulses LB0 at the wavelength $\lambda_0$ are generated only when the indicator signal S2($t$) indicates that an object O1 is properly present in the sample region. Consequently, substantially all spectra measured by the detector 100 may be object-related spectra. In this operating mode, substantially all spectra measured by the detector 100 may be classified to be object-related spectra.

One or more objects O1, O2, O3 may move through the sample region REG1 e.g. at a time to such that the indicator signal S2($t$) does not exceed the threshold limit LIM1. The apparatus 500 may be arranged to operate such that a low peak of the indicator signal S2($t$) does not trigger generation of an illuminating light pulse LB0.

In this case, all Raman scattered light pulses $LB1_R$ detected by the detector 100 may consist of light pulses $LB1_R$ which are obtained from the sample region REG1 when the indicator signal S2($t$) indicates that an object O1 is located in the sample region REG1. A first output spectrum F($\lambda$) may be formed from the spectral intensity distribution I($\lambda$) of a first group of Raman scattered light pulses $LB1_R$. Substantially all Raman scattered light pulses $LB1_R$ may belong to said first group in a situation where the light source LS1 is triggered when the apparatus 500 detects the presence of an object in the sample region REG1.

The method may comprise forming a first output spectrum F1($\lambda$) from the spectral intensity distribution I($\lambda$) of a first group of Raman scattered light pulses $LB1_R$, wherein the pulses of said first group of Raman scattered light pulses $LB1_R$ are obtained from the sample region (REG1) when the indicator signal S2($t$) indicates that an object O1 is located in the sample region REG1.

The method may comprise:
generating triggered illuminating light pulses LB0 by triggering an illuminating light source LS1 based on the indicator signal S2($t$), and
forming the output spectrum F1($\lambda$) from the spectral intensity distribution I($\lambda$) of Raman scattered light pulses $LB1_R$ obtained when the sample region REG1 is illuminated by said triggered illuminating light pulses LB0.

The apparatus 500 may also be configured to detect when the indicator signal S2($t$) is lower than a (second) threshold value LIM2. When the indicator signal S2($t$) is lower than the threshold value LIM2, this may be interpreted to be an indication that no object is overlapping the sample region REG1. When the indicator signal S2($t$) is lower than the value LIM2, this may be interpreted to be an indication that substantially 100% of the Raman-scattered radiation is emitted from the medium LIQ1. When the aim is to analyze the medium LIQ1, an output spectrum F2($\lambda$) may be formed (only) from the spectral intensity of the Raman-scattered light pulses LB1 which are obtained when the indicator signal S2($t$) is lower than the value LIM2. The apparatus 500 may be arranged to operate such that the light pulses LB0 are triggered only when the indicator signal S2($t$) is lower than the value LIM2. Consequently, the contribution of the objects O1, O2, O3 to the output spectrum F2($\lambda$) may be reduced or eliminated. Using the limit LIM2 may ensure that the sample region REG1 is free from objects. Consequently, substantially all spectra measured by the detector 100 may be medium-related spectra. In this operating mode, substantially all spectra measured by the detector 100 may be medium-related spectra.

The apparatus 500 may be arranged to provide the timing signal S3($t$) and/or the control signal S4($t$) to the detector 100 also when the light source LS1 operates in the triggered mode, i.e. when the light pulses LB0 are generated according to the trigger signal S0. Using the timing signal S3($t$) and/or the control signal S4($t$) may facilitate precise timing of operation the detector 100.

The auxiliary light source LS5 may also be used for detecting the presence of the objects when the illuminating light source LS1 operates at a substantially constant repetition rate. The auxiliary light source LS5 may also be used when the measured data is classified according to the indicator signal S2(t).

The apparatus 500 may optionally comprise e.g. an optical filter to define a spectral passband for auxiliary the detector DET2. When using the auxiliary light source LS5, the optical filter may be arranged to operate such that scattered light LB6 at the wavelength $\lambda_A$ may pass to the detector DET2, wherein the optical filter may be arranged to prevent propagation of scattered light LB6 at the wavelength $\lambda_0$ to the detector DET2. The optical filter may be e.g. an interference filter positioned between the beam splitter and the detector DET2. Also the beam splitter BS1 may be arranged to operate as the optical filter.

Figure 6A:
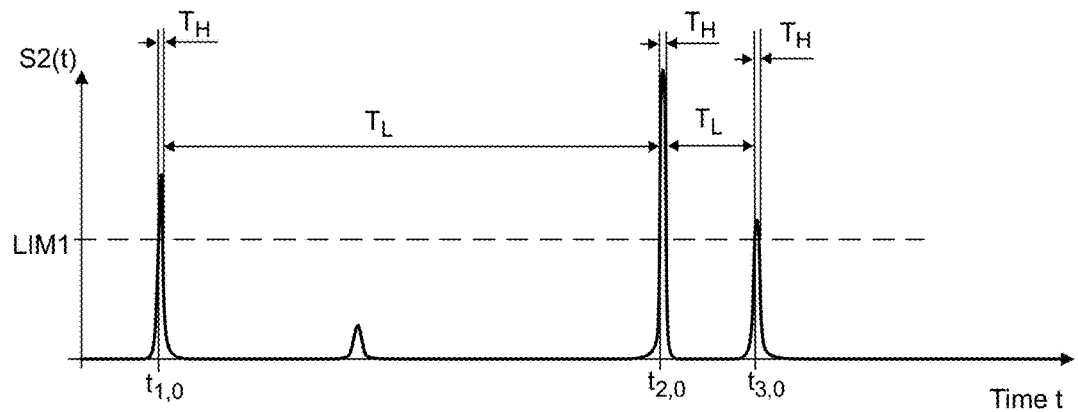
FIG. 6a shows, by way of example, estimating the volume fraction of objects by determining a duty cycle from the indicator signal.

Referring to FIG. 6a, the volume fraction of the objects O1, O2, O3 may be estimated from the indicator signal S2(t). The indicator signal S2(t) of FIG. 6a may be provided e.g. by using the auxiliary light LB5. The method may comprise estimating the volume fraction of the objects O1, O2, O3 in the heterogeneous substance MX based on the indicator signal S2(t). $T_H$ may denote the duration of a time period when the indicator signal S2(t) is higher than or equal to a predetermined limit LIM1. $T_L$ may denote the duration of a time period when the indicator signal S2(t) is lower than said predetermined limit LIM1. The ratio $T_H/(T_L+T_H)$ may be indicative of the volume fraction of the objects O1, O2, O3 in the heterogeneous substance MX. The ratio $T_H/(T_L+T_H)$ may be called e.g. as the duty cycle. The ratio $T_H/(T_L+T_H)$ may be indicative of the number density of the objects O1, O2, O3 in the heterogeneous substance MX. The ratio $T_H/(T_L+T_H)$ may be indicative of the concentration of the objects O1, O2, O3 in the heterogeneous substance MX.

The method may comprise estimating the volume fraction of the objects by determining the duty cycle $T_H/(T_L+T_H)$ from the indicator signal S2(t).

The volume fraction of the objects means the ratio $V_{OBJ}/V_{TOT}$, where $V_{TOT}$ means a total volume of the heterogeneous substance MX, and $V_{OBJ}$ means the sum of the volumes of the objects O1, O2, O3 contained in said total volume $V_{TOT}$.

Figure 6B:
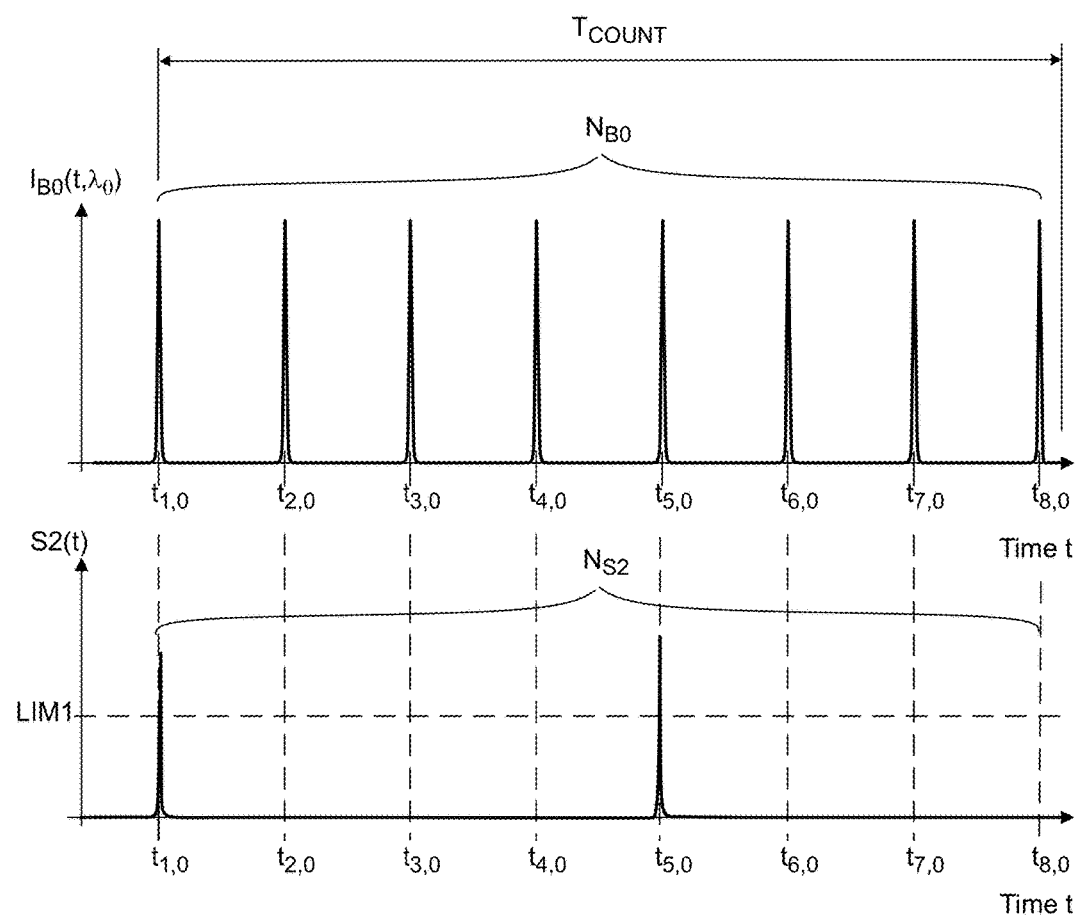
FIG. 6b shows, by way of example, estimating the volume fraction of objects by counting the number of illuminating light pulses and by counting the number of indicator signal pulses.

Referring to FIG. 6b, the volume fraction of the objects O1, O2, O3 may be estimated from the indicator signal S2(t) also when indicator signal S2(t) is formed by monitoring the intensity of the elastically scattered light at the wavelength $\lambda_0$ of the illuminating light pulses LB0. $T_{COUNT}$ may denote the duration of a counting period. $N_{B0}$ may denote the number of light pulses LB0 generated during the counting period $T_{COUNT}$. $N_{S2}$ may denote the number of pulses of the indicator signal S2(t) which exceed the predetermined limit LIM1 during said counting period $T_{COUNT}$. The ratio $N_{S2}/N_{B0}$ may be indicative of the volume fraction of the objects O1, O2, O3. The method may comprise estimating the volume fraction of the objects by determining the ratio $N_{S2}/N_{B0}$. This ratio may be determined also when the illuminating light pulses LB0 are generated at regular intervals.

The duration of the counting period $T_{COUNT}$ may be e.g. in the range of 1 s to 1000 s. The number $N_{B0}$ of illuminating pulses LB0 generated during the counting period $T_{COUNT}$ may be e.g. in the range of $10^2$ to $10^9$.

The indicator signal S2(t) may be provided by illuminating the sample region REG1 with the illuminating light pulses LB0, and by monitoring the intensity $I_{LB1}(t,\lambda_0)$ of elastically scattered light $LB1_R$ gathered from the sample region REG1.

The indicator signal S2(t) may also be provided by illuminating the sample region REG1 with auxiliary light LB5 having an auxiliary wavelength $\lambda_A$, and monitoring the intensity of elastically scattered light LB6 obtained from the sample region REG1 at said auxiliary wavelength $\lambda_A$. The auxiliary wavelength $\lambda_A$ may be longer than the longest wavelength of the collected Raman spectrum so that the scattering of the auxiliary light LB5 does not disturb the measurement of the Raman spectrum.

The method may comprise controlling timing of the illuminating light pulses LB0 based on the indicator signal S2(t) and/or the method may comprise forming an output spectrum by classifying the Raman scattered light pulses $LB1_R$ according to the indicator signal S2(t).

The method may comprise:
varying composition at a sample region (REG1),
providing an indicator signal (S2) indicative of elastic scattering coefficient of the sample region,
illuminating the sample region (REG1) with illuminating light pulses (LB0),
controlling timing of illuminating light pulses (LB0) based on the indicator signal (S2(t)), and
forming one or more output signal values (F1(λ)) by measuring the spectral intensity distribution (I(λ)) of Raman scattered light pulses excited by the illuminating light pulses (LB0) in the sample region (REG1).

The time interval between consecutive light pulses LB0 may be substantially irregular when controlling the timing of illuminating light pulses (LB0) based on the indicator signal (S2(t)).

The method may comprise:
varying composition at a sample region (REG1),
providing an indicator signal (S2(t)) indicative of elastic scattering coefficient of the sample region (REG1),
illuminating the sample region (REG1) with illuminating light pulses (LB0),
obtaining Raman signal values ($b(\lambda_k)$) by measuring the spectral intensity distribution (I(λ)) of Raman scattered light pulses ($LB1_R$) excited by the illuminating light pulses (LB0) in the sample region (REG1), and
forming one or more output signal values (F1(λ)) by classifying the Raman signal values ($b(\lambda_k)$) according to the indicator signal (S2(t)).

The time interval between consecutive light pulses LB0 may be substantially regular when the output signal values (F1(λ)) are formed by classifying the Raman signal values ($b(\lambda_k)$) according to the indicator signal (S2(t)). The light pulses LB0 may be produced at a substantially constant repetition rate.

The method may comprise classifying the measured Raman signal values to a first category and/or to a second category according to the indicator signal, wherein Raman signal values of the first category may be associated with (dense) objects O1, O2, O3. Raman signal values of the second category may be associated with the medium LIQ1.

The Raman scattered light pulses $LB1_R$ may be classified to belong to a first category and/or to a second category based on the signal level of the indicator signal (S2). A first Raman scattered light pulse $LB1_R$ may be classified to belong to the first category if the signal level of the indicator signal (S2) is higher than a predetermined limit LIM1 when said first Raman scattered light pulse $LB1_R$ is emitted from the sample region REG1. Thus, the indicator signal (S2) indicates the presence of an object O1 in the sample region REG1, and said first Raman scattered light pulse $LB1_R$ may be classified to belong to the first category. The measured spectral data (I(λ)) of said first Raman scattered light pulse (LB1$_R$) may be classified to belong to the first category. Raman signal values determined from the first Raman scattered light pulse (LB1$_R$) may be classified to belong to the first category.

The spectral data of the first category may be interpreted to indicate mainly the spectral properties of the objects O1, O2, O3. The spectral data of the first category may be object-related.

A first output spectrum F1 ($\lambda$) may be subsequently formed from the spectral data of the first category. The first output spectrum F1($\lambda$) may be formed e.g. by averaging the Raman spectrum (I($\lambda$)) of two or more pulses LB1$_R$ of the first category.

A second Raman scattered light pulse LB1$_R$ may be classified to belong to the second category if the signal level of the indicator signal (S2) is lower than a predetermined limit LIM1 when said second Raman scattered light pulse LB1$_R$ is emitted from the sample region REG1. Thus, the indicator signal (S2) may indicate that an object is not present in the sample region (REG1), and said second Raman scattered light pulse LB1$_R$ may be classified to belong to the second category. The measured spectral data (I($\lambda$)) of said second Raman scattered light pulse (LB1$_R$) may be classified to belong to the second category. Raman signal values determined from the second Raman scattered light pulse (LB1$_R$) may be classified to belong to the second category. The spectral data of the second category may be interpreted to indicate mainly the spectral properties of the medium LIQ1. The spectral data of the second category may be medium-related.

A second output spectrum F2($\lambda$) may be subsequently formed from the spectral data of the second category. The first output spectrum F1($\lambda$) may be formed e.g. by averaging the Raman spectrum (I($\lambda$)) of two or more pulses LB1$_R$ of the first category.

The spectral intensity distribution (I($\lambda$)) of the Raman scattered light pulses LB1$_R$ may be measured with an array of detectors, wherein the operation of the detectors may be temporally synchronized with the illuminating light pulses. The detectors may be time-gated according to the timing of the illuminating light pulses.

Figure 7:
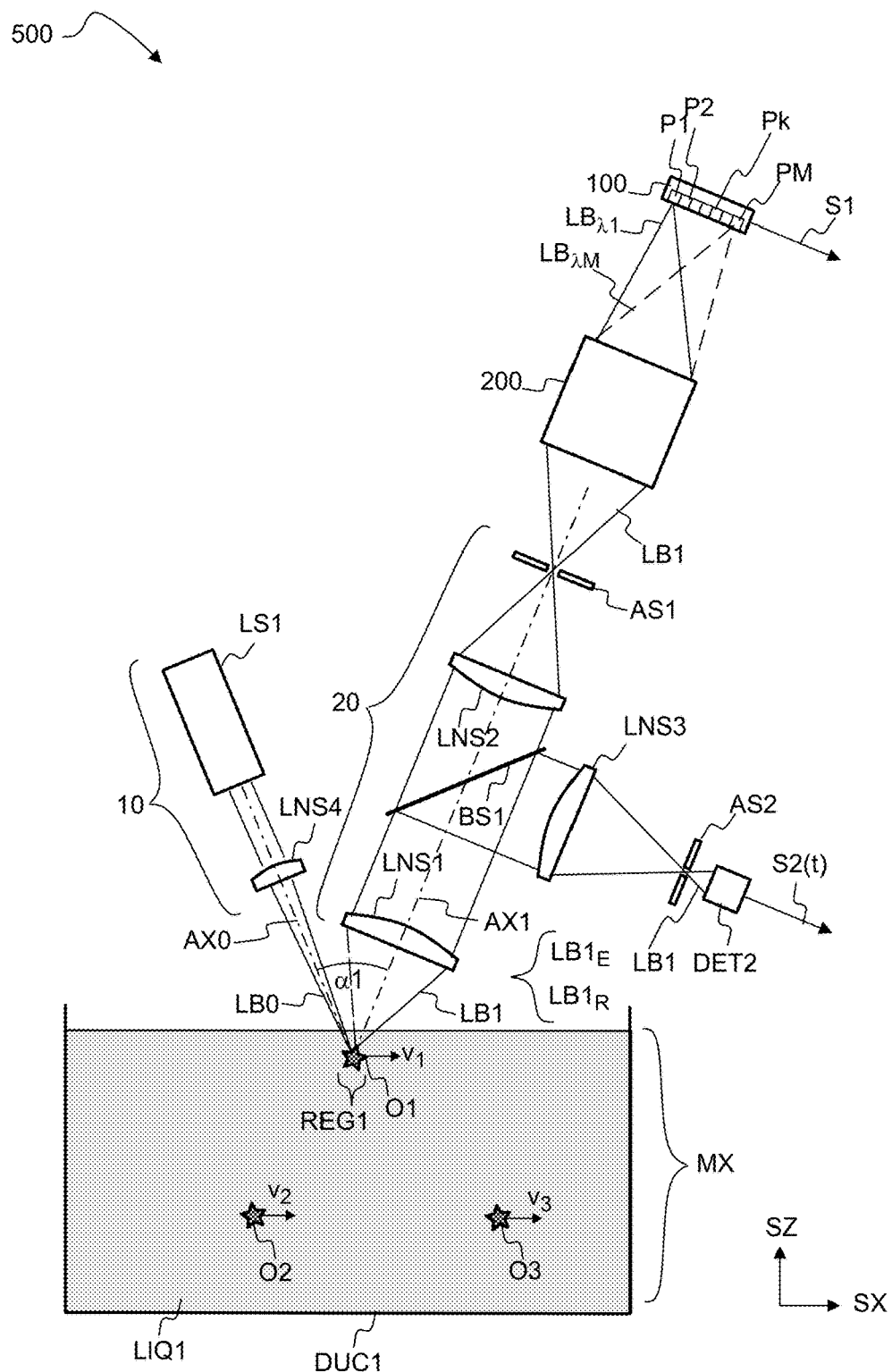
FIG. 7 shows, by way of example, an apparatus, where the optical axis of illuminating optics crosses the optical axis of light gathering optics.

Referring to FIG. 7, illumination of the sample region REG1 and gathering of the light from the sample region REG1 may also take place such that the optical axis AX0 of the illuminating optics 10 may cross the optical axis AX1 of the light gathering optics 20. The apparatus 500 may comprise a lens LNS4 for focusing illuminating light LB0 to the sample region REG1. The illuminating optics 10 may have a first optical axis AX0, and the light gathering optics 20 may have a second optical axis AX1. The angle $\alpha$1 denotes the angle between the optical axis AX0 and AX1. The angle $\alpha$1 may be different from zero. The illuminating light LB0 and the scattered light LB1 may pass through one or more interfaces, which may refract light. For example, the light may pass through an interface between a window 50 and the substance MX. For example, the light may pass through an interface between air and the substance MX. Refraction at the interface may change the direction of propagation of light. The apparatus 500 may be arranged to take into consideration the refraction at the one or more interfaces such that the focus of the illuminating light may coincide with the position of the sample region REG1.

In the confocal arrangement (e.g. as shown in FIGS. 1a-1c and in FIG. 4), the optical axis AX0 may coincide with the optical axis AX1. In particular, the optical axis AX0 may be substantially parallel with the optical axis AX1. In this case, illumination and gathering of light may take place through the same relatively small window 50. Consequently, it may be relatively easy to arrange the optical access e.g. to an industrial process vessel or duct DUC1. The confocal arrangement may also be relatively insensitive to a positioning error of the lens LNS1 with respect to said window 50.

Figure 8A:
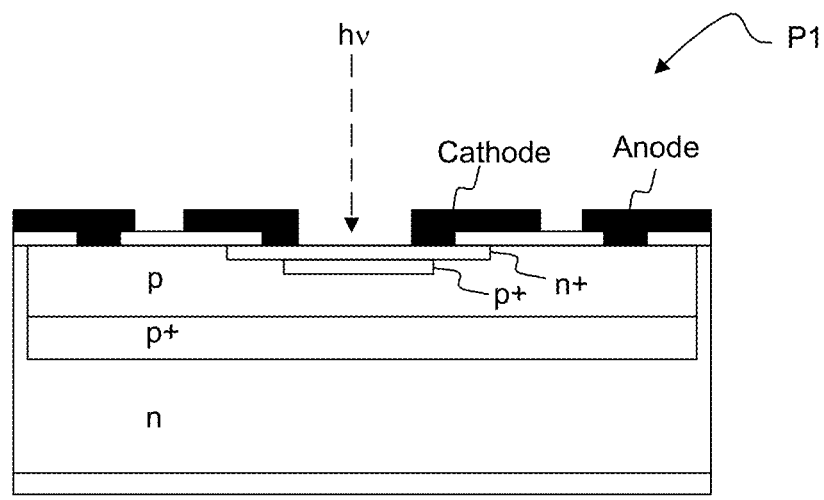
FIG. 8a shows, by way of example, a single photon avalanche diode.

Referring to FIG. 8a, the detector 100 may comprise one or more detector pixels P1, P2, . . . . A detector pixel P1, P2 may comprise a single photon avalanche diode (SPAD). In particular, a detector pixel P1, P2 may comprise a CMOS SPAD. CMOS is an acronym for Complementary Metal Oxide Semiconductor. The single photon avalanche diode may also be called e.g. as a Geiger mode avalanche photodiode. The single photon avalanche diode comprises a p-n junction, which may be reverse-biased such that a single charge carrier injected into the depletion layer of the p-n junction may trigger a self-sustaining avalanche. The single charge carrier may be generated by a photon hv. In the beginning of the avalanche, the current through the p-n junction may rapidly rise so that the leading edge of the avalanche current pulse may mark the arrival time of the detected photon hv. The rapid chance of the current through the p-n may be detected by a suitable electronic circuit. The current through the p-n junction may continue until the avalanche is quenched. The single photon avalanche diode may be used together with a quenching circuit, which may be arranged to quench an avalanche current caused by a photon. The single photon avalanche diode may be used together with a quenching circuit, which may be arranged to quench an avalanche current caused by a photon. The apparatus 500 may comprise an electronic unit, which may be arranged to detect a rapid chance of the avalanche current and also to quench the avalanche current. Thus, a single photon avalanche diode may comprise a reverse-biased p-n junction, wherein each photon hv impinging on an active area of the single photon avalanche diode may be arranged cause a detectable current pulse with a probability, which is substantially greater than zero. The detection probability may also be called e.g. as a quantum efficiency. The quantum efficiency of the single photon avalanche diode may be e.g. greater than 20% for photons hv in a predetermined wavelength range. The quantum efficiency of a single photon avalanche diode may be e.g. greater than 20% for photons in the range of 400 nm to 900 nm.

Figure 8B:
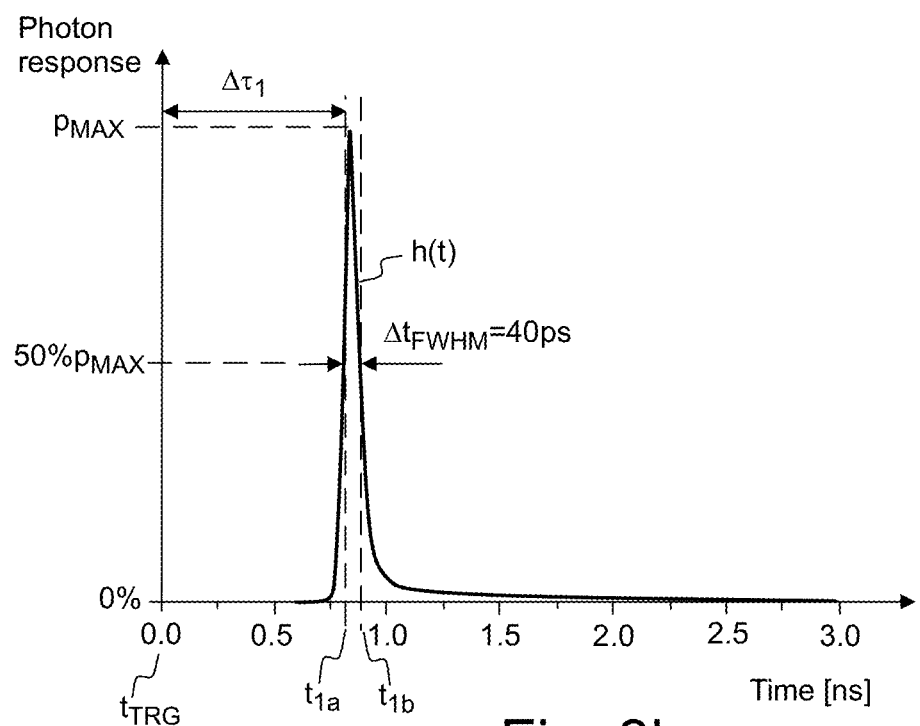
FIG. 8b shows, by way of example, temporal evolution of the probability of detecting photons when using a time-gated detector.

FIG. 8b shows, by way of example, a temporal response function h(t) of a single photon avalanche diode. The response function h(t) may also be called e.g. as the single photon response of the single photon avalanche diode. The temporal width $\Delta t_{FWHM}$ of the response function h(t) may be e.g. shorter than or equal to 60 ps. For example, the temporal width $\Delta t_{FWHM}$ of the response function h(t) may be e.g. in the range of 35 ps to 50 ps. For example, the temporal width $\Delta t_{FWHM}$ may be substantially equal to 40 ps. The apparatus 500 may comprise a delay unit for controlling a time delay $\Delta t_1$. The time delay $\Delta t_1$ may denote e.g. a difference between the time $t_{1a}$ of the rising edge of the temporal response function h(t) and the time $t_{TRG}$ Of arrival of a trigger pulse $S_{TRG}$ to the detector 100.

The temporal response function h(t) may also be interpreted to represent the probability of detecting a photon per unit time. The probability of detecting a photon per unit time may reach a maximum value $p_{MAX}$. The probability of detecting a photon per unit time may reach 50% of the maximum value $p_{MAX}$ at the times $t_{1a}$, $t_{1b}$. For example, the integrated area of the response function h(t) between the times $t_{1a}$, $t_{1b}$ may correspond e.g. to a probability of 10% for detecting a photon, which impinges on a predetermined detector pixel P1 during the time period between the times $t_{1a}$, $t_{1b}$. The temporal width $\Delta t_{FWHM}$ of the response function h(t) may be determined e.g. by calculating the difference $t_{1b}-t_{1a}$. The function h(t) may represent the temporal response function h(t) of a single photon avalanche diode regarding a single detection period. The function h(t) may represent the temporal response function h(t) of a single photon avalanche diode regarding a single detection period. The function h(t) may represent the probability of detecting a photon per unit time when counting photons for a single detection period. The function h(t) may represent the probability of detecting a photon per unit time when counting photons of light LB1 emitted from the sample region REG1 during a time period at a given wavelength λ.

The apparatus 500 may comprise one or more counting units for counting the number of photons detected by a detector pixel P1. The apparatus 500 may comprise one or more counting units for counting the number of photons detected by a second detector pixel P2. In an embodiment, the detector pixels P1, P2 and the counting units may be implemented on the same (semiconductor) substrate. The counting units may be implemented e.g. by means of a computer program running on one or more data processors and/or by means of electronic circuits implemented on a substrate.

The apparatus 500 may comprise a counting unit, which may be arranged to count the number of photons detected by a detector pixel P1 when the sample is illuminated by several light pulses LB0. The counting unit may be arranged to change a counter value each time when a single detector pixel P1 detects a photon during a predetermined (integration) time period. The time period may be precisely timed with respect to the trigger pulse $S_{TRG}$. A counting unit may be arranged to change a counter value each time when the single detector pixel P1 detects a photon during a predetermined time period.

For each illuminating light pulse LB0, the single detector pixel P1 may detect only one photon. The operating parameters of the apparatus 500 may be selected such that the probability of detecting a photon may be e.g. in the range of 0.01% to 10% when the sample region REG1 is illuminated by a single light pulse LB0.

$N_{P1}$ may denote the number of photons detected by a detector pixel P1. $N_{LB0}$ may denote the number of light pulses LB0. The light source LS1 may be arranged to provide $N_{LB0}$ illuminating light pulses LB0 during a time period $T_{SEQ}$. The number $N_{LB0}$ may be e.g. in the range of $10^2$ to $10^6$. The time period $T_{SEQ}$ may be e.g. in the range of 1 ms to 1000 s. The intensity of the illuminating light pulses, the duration of the light pulses and the light gathering efficiency of the gathering optics 20 may be selected such that the ratio $N_{P1}/N_{LB0}$ may be e.g. in the range of 0.01% to 10%.

If the ratio $N_{P1}/N_{LB0}$ is too low, the total time needed to measure the Raman spectrum may be excessively long. If the ratio $N_{P1}/N_{LB0}$ is too high, the measured values b1, b2, b3 are not proportional to the intensity of the scattered light LB1, i.e. the relationship between the intensity of the scattered light LB1 and the measured values b1, b2, b3 become nonlinear. Advantageously, the ratio $N_{P1}/N_{LB0}$ may be e.g. smaller than or equal to 1%.

Figure 8C:
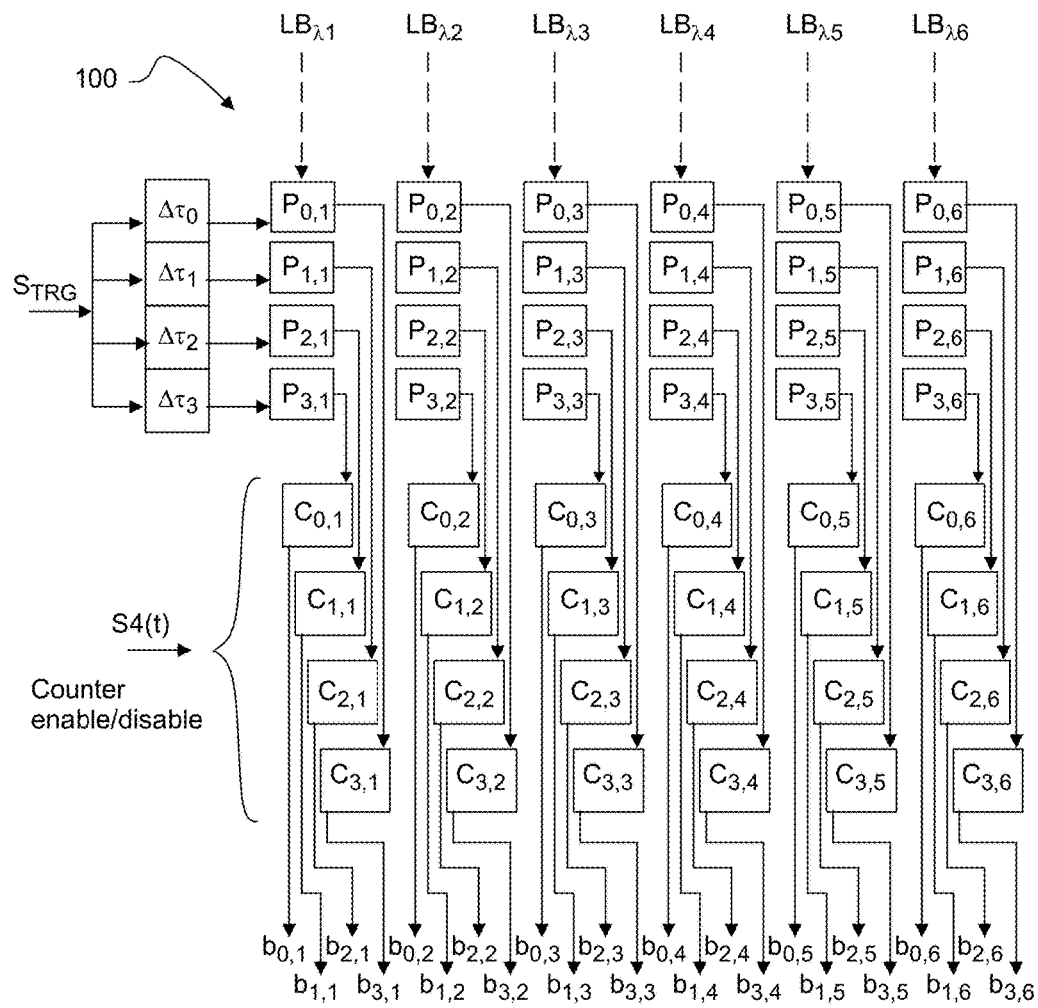
FIG. 8c shows, by way of example, a detector array, which comprises an array of single photon avalanche diodes.

Referring to FIG. 8c, the detector 100 may comprise a pixel $P_{0,1}$ for detecting a photon at a wavelength $\lambda_1$ during a first integration time period, a pixel $P_{1,1}$ for detecting a photon at a wavelength $\lambda_1$ during a second integration time period, a pixel $P_{2,1}$ for detecting a photon at a wavelength $\lambda_1$ during a third time period, and a pixel $P_{3,1}$ for detecting a photon at a wavelength $k_1$ during a fourth time period. The detector 100 may comprise a counting unit $C_{0,1}$ arranged to provide a measured signal $b_{0,1}$ by counting photons detected by the pixel $P_{0,1}$. The detector 100 may comprise a counting unit $C_{1,1}$ arranged to provide a signal $b_{1,1}$ by counting photons detected by the pixel $P_{1,1}$. The detector 100 may comprise a counting unit $C_{2,1}$ arranged to provide a signal $b_{2,1}$ by counting photons detected by the pixel $P_{2,1}$. The detector 100 may comprise a counting unit $C_{3,1}$ arranged to provide a signal $b_{3,1}$ by counting photons detected by the pixel $P_{3,1}$.

The detector 100 may comprise a pixel $P_{0,2}$ for detecting a photon at a wavelength $\lambda_2$ during the first integration time period, a pixel $P_{1,2}$ for detecting a photon at a wavelength $\lambda_2$ during the second integration time period, a pixel $P_{2,2}$ for detecting a photon at a wavelength $\lambda_2$ during the third integration time period, and a pixel $P_{3,2}$ for detecting a photon at a wavelength $\lambda_2$ during a third integration time period. The detector 100 may comprise a counting unit $C_{0,2}$ arranged to provide a signal $b_{0,2}$ by counting photons detected by the pixel $P_{0,2}$. The detector 100 may comprise a counting unit $C_{1,2}$ arranged to provide a signal $b_{1,2}$ by counting photons detected by the pixel $P_{1,2}$. The detector 100 may comprise a counting unit $C_{2,2}$ arranged to provide a signal $b_{2,2}$ by counting photons detected by the pixel $P_{2,2}$. The detector 100 may comprise a counting unit $C_{3,2}$ arranged to provide a signal $b_{3,2}$ by counting photons detected by the pixel $P_{3,2}$.

The detector 100 may comprise pixels P and counters C for providing measured signals b in a corresponding way at further wavelengths $\lambda_3$, $\lambda_4$, $\lambda_5$, $\lambda_6$, . . . . The detector 100 may comprise pixels P and counters C e.g. for measuring the spectral intensity at the different wavelength bands having the central wavelengths $\lambda_1$, $\lambda_2$, . . . $\lambda_k$, $\lambda_{k+1}$, . . . $V_M$. The detector 100 may comprise pixels P for measuring the spectral intensity e.g. at 1024 adjacent wavelength bands.

The timing of the first, second, third and fourth integration time periods with respect to the trigger signal $S_{TRG}$ may be controlled e.g. by delays $\Delta\tau_0$, $\Delta\tau_1$, $\Delta\tau_2$, $\Delta\tau_3$. The detector 100 or the apparatus 500 may comprise delay units for providing the delays $\Delta\tau_0$, $\Delta\tau_1$, $\Delta\tau_2$, $\Delta\tau_3$.

In an embodiment, the signals $b_{0,1},b_{1,1},b_{2,1},b_{3,1}$ may also be provided by using a single photon avalanche diode (e.g. $P_{0,1}$). In an embodiment, the signals $b_{0,1},b_{1,1},b_{2,1},b_{3,1}$ may also be provided by using a single photon avalanche diode (e.g. $P_{0,1}$) and by using the counting units $C_{0,1}$, $C_{1,1}$, $C_{2,1}$, $C_{3,1}$. For example, the counting unit $C_{0,1}$ may be arranged to provide a signal value $b_{0,1}$ by counting photons detected by the single photon avalanche diode $P_{0,1}$ during the first integration time period, the counting unit $C_{1,1}$ may be arranged to provide a signal value $b_{1,1}$ by counting photons detected by the single photon avalanche diode $P_{0,1}$ during the second integration time period, the counting unit $C_{2,1}$ may be arranged to provide a signal value $b_{2,1}$ by counting photons detected by the single photon avalanche diode $P_{0,1}$ during the third integration time period, and the counting unit $C_{3,1}$ may be arranged to provide a signal value $b_{3,1}$ by counting photons detected by the single photon avalanche diode $P_{0,1}$ during the third integration time period. For example, the detector 100 or the control unit CNT1 may comprise a memory MEM3 for storing values of the signals $b_{0,1},b_{1,1},b_{2,1},b_{3,1}$.

The signals $b_{0,2},b_{1,2},b_{2,2},b_{3,2}$ may also be provided by using the single photon avalanche diode (e.g. $P_{0,2}$). The signals $b_{0,3},b_{1,3},b_{2,3},b_{3,3}$ may also be provided by using the single photon avalanche diode (e.g. $P_{0,3}$). The signals $b_{0,4}$, $b_{1,4},b_{2,4},b_{3,4}$ may also be provided by using the single photon avalanche diode (e.g. $P_{0,4}$). The signals $b_{0,5},b_{1,5},b_2,$ $b_{3,5}$ may also be provided by using the single photon avalanche diode (e.g. $P_{0,5}$). The signals $b_{0,6}, b_{1,6}, b_{2,6}, b_{3,6}$ may also be provided by using the single photon avalanche diode (e.g. $P_{0,6}$).

The detector 100 may be arranged to operate such that the counters C may be enabled and disabled based on a control signal $S4(t)$. The control signal $S4(t)$ may be determined from the indicator signal $S2(t)$ e.g. as discussed with reference to FIG. 1c.

The detector 100 may optionally comprise a first set of counters C and a second set of counters C. The detector 100 may be arranged to operate such that the counters C of the second set are disabled when the counters C of the first set are enabled. The detector 100 may be arranged to operate such that the counters C of the second set are enabled when the counters C of the first set are disabled. Also in this case the counters C may be enabled and disabled according to the control signal $S4(t)$. Thus, the first set of counters C may be arranged to provide Raman spectrum values $b(\lambda)$ associated with the objects O1, O2, O3, and the second set of counters C may be arranged to provide Raman spectrum values $b(\lambda)$ associated with the carrier medium LIQ1.

Figure 8D:
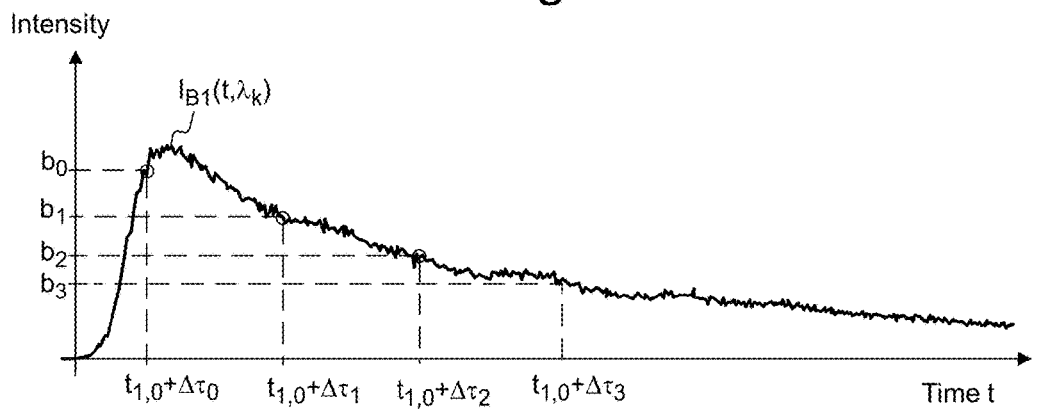
FIG. 8d shows, by way of example, temporal evolution of intensity of Raman scattered light obtained from the sample region.

FIG. 8d shows, by way of example, temporal evolution of the intensity $I_{B1}(t,\lambda_k)$ of inelastically scattered light obtained from the sample region REG1 at a given wavelength $\lambda_k$.

The intensity $I_{B1}(t,\lambda_k)$ may have a value b0 at a time $t_{1,0}+\Delta\tau_0$. The intensity $I_{B1}(t,\lambda_k)$ may have a value $b0(\lambda_k)$ at a time $t_{1,0}+\Delta\tau_0$. The intensity $I_{B1}(t,\lambda_k)$ may have a value $b1(\lambda_k)$ at a time $t_{1,0}+\Delta\tau_1$. The intensity $I_{B1}(t,\lambda_k)$ may have a value $b2(\lambda_k)$ at a time $t_{1,0}+\Delta\tau_2$. The intensity $I_{B1}(t,\lambda_k)$ may have a value $b3(\lambda_k)$ at a time $t_{1,0}+\Delta\tau_3$. The value b0 may be obtained e.g. from a SPAD detector 100.

The values b0, b1 may be obtained from a SPAD detector 100. The values b0, b1, b2, b3 may be obtained e.g. from a SPAD detector 100.

The intensity $I_{B1}(t,\lambda_k)$ may also comprise a contribution of fluorescence in addition to the Raman scattered light. The contribution of the fluorescence may be estimated e.g. from one or more of the measured intensity values b1, b2, b3. The estimated contribution of the fluorescence may be subsequently eliminated from the measured intensity value b0.

In an embodiment, the method may further comprise providing an auxiliary signal indicative of fluorescence emitted from the sample region REG1. The method may comprise determining the type of a particle (i.e. object) based on fluorescence spectrum of said particle.

The sample region REG1 may also be illuminated with auxiliary illuminating light which has a suitable wavelength for stimulating inelastic fluorescence emission in a material located in the sample region REG1. The wavelength of the auxiliary illuminating light may be selected such that the stimulated inelastic fluorescence emission does not spectrally overlap with the collected Raman spectrum. The intensity of the fluorescence emission may be monitored by an auxiliary detector. Monitoring the intensity of the stimulated fluorescence emission may provide additional information about the objects O1, O2, O3 and/or the carrying medium LIQ1. When using pulsed auxiliary light, the fluorescence emission may be delayed with respect to a pulse of the auxiliary light. In particular, when using pulsed auxiliary light, monitoring the temporal behavior of the stimulated fluorescence emission may provide additional information about the objects O1, O2, O3 and/or the carrying medium LIQ1. Monitoring the fluorescence may provide additional information in addition to monitoring the elastically scattered light. Monitoring the fluorescence may provide additional information in addition to the indicator signal $S2(t)$.

In an embodiment, the method may further comprise providing an auxiliary signal indicative of angular distribution of the elastic scattering coefficient of the sample region REG1. The method may comprise determining the type of a particle (i.e. object) based on angular intensity distribution of elastically scattered light obtained said particle.

In an embodiment, a chemical process or a cell culture process may be controlled based on a Raman spectrum measured by the apparatus 500. A chemical process or a cell culture process may be controlled based on a Raman spectrum measured by the method, which comprises classifying or triggering based on the indicator signal.

The measuring apparatus 500 may be arranged to provide an output spectrum $F1(\lambda)$ and/or $F2(\lambda)$ according the method and/or according to the versions discussed above.

In an embodiment, triggering the illuminating light pulses LB0 and/or classification of measured Raman signal data may also be performed based on information about the fluorescence. Generation of the illuminating light pulses LB0 and/or classification of measured Raman signal data may be performed e.g. based on a signal indicative of fluorescence cross section of the sample region.

Various aspects of the invention are illustrated by the following examples.

Example 1

A method for measuring Raman scattering, the method comprising:
varying composition in a sample region (REG1),
providing an indicator signal (S2) indicative of elastic scattering coefficient of the sample region (REG1),
illuminating the sample region (REG1) with illuminating light pulses (LB0), and
forming a first output spectrum ($F1(\lambda)$) from the spectral intensity distribution ($I(\lambda)$) of a first group of Raman scattered light pulses ($LB1_R$), wherein the pulses of said first group of Raman scattered light pulses ($LB1_R$) are obtained from the sample region (REG1) when the indicator signal ($S2(t)$) indicates that an object (O1) is located in the sample region (REG1).

Example 2

The method of example 1, comprising:
generating triggered illuminating light pulses (LB0) by triggering an illuminating light source (LS1) based on the indicator signal ($S2(t)$), and
forming the first output spectrum ($F1(\lambda)$) from the spectral intensity distribution ($I(\lambda)$) of Raman scattered light pulses ($LB1_R$) obtained when the sample region (REG1) is illuminated by said triggered illuminating light pulses (LB0).

Example 3

The method of example 1 or 2, comprising changing the state of a trigger signal (S0) for triggering the illuminating light source (LS1) when the indicator signal (S2) exceeds a predetermined level (LIM1).

Example 4

The method of example 1, comprising
determining whether a Raman scattered light pulse ($LB1_R$) belongs to a first category or not, wherein the Raman scattered light pulse ($LB1_R$) is determined to belong to the first category only if the indicator signal (S2) exceeds a predetermined level (LIM1) when the Raman scattered light pulse ($LB1_R$) is obtained from the sample region (REG1), and forming the first output spectrum ($F1(\lambda)$) from the spectral intensity distribution ($I(\lambda)$) of Raman scattered light pulses ($LB1_R$) of the first category.

Example 5

The method of example 1, comprising determining whether a Raman scattered light pulse ($LB1_R$) belongs to a first category or to a second category based on the indicator signal (S2), wherein the Raman scattered light pulse ($LB1_R$) is determined to belong to the first category if the indicator signal (S2) exceeds a predetermined level (LIM1) when the Raman scattered light pulse ($LB1_R$) is obtained from the sample region (REG1), and wherein the Raman scattered light pulse ($LB1_R$) is determined to belong to the second category if the indicator signal (S2) is lower than said predetermined level (LIM1) when the Raman scattered light pulse ($LB1_R$) is obtained from the sample region (REG1), forming the first output spectrum ($F1(\lambda)$) from the spectral intensity distribution ($I(\lambda)$) of Raman scattered light pulses ($LB1_R$) of the first category, and forming a second output spectrum ($F2(\lambda)$) from the spectral intensity distribution ($I(\lambda)$) of Raman scattered light pulses ($LB1_R$) of the second category.

Example 6

The method according to any of the examples 1 to 5, wherein the spectral intensity distribution ($I(\lambda)$) of the Raman scattered light pulses ($LB1_R$) is measured by a detector (100), and the method comprises controlling operation of the detector (100) based on the indicator signal ($S2(t)$).

Example 7

The method according to any of the examples 1 to 6, wherein the spectral intensity distribution ($I(\lambda)$) of the Raman scattered light pulses ($LB1_R$) is measured by a detector (100), and the method comprises enabling operation of the detector (100) based on the indicator signal ($S2(t)$).

Example 8

The method according to any of the examples 1 to 6, wherein the spectral intensity distribution ($I(\lambda)$) of the Raman scattered light pulses ($LB1_R$) is measured by using an array (100) of single photon avalanche photodiodes and a set of counters arranged to count pulses provide by the photodiodes, wherein operation of said set of counters is enabled based on the indicator signal $S2(t)$.

Example 9

The method according to any of the examples 1 to 5, wherein the composition is varied by moving a heterogeneous substance (MX) with respect to the sample region (REG1), and the heterogeneous substance (MX) comprises a plurality of objects (O1, O2, O3) suspended in a carrier medium (LIQ1).

Example 10

The method according to any of the examples 1 to 9 comprising estimating a volume fraction of objects (O1, O2, O3) based on the indicator signal ($S2(t)$).

Example 11

The method according to any of the examples 1 to 10, wherein the illuminating light pulses (LB0) are focused to the sample region (REG1) through a first lens (LNS1), and the Raman scattered light ($LB1_R$) from the sample region (REG1) is gathered through said first lens (LNS1).

Example 12

An apparatus (500), comprising:
an illuminating light source (LS1) and illuminating optics (10) arranged to illuminate a sample region (REG1) with illuminating light pulses (LB0),
light gathering optics (20) to gather Raman scattered light pulses ($LB1_R$) from the sample region (REG1),
a spectral disperser (200) and a detector array (100) for measuring the spectral intensity distribution ($I(\lambda)$) of Raman scattered light pulses ($LB1_R$) obtained from the sample region (REG1),
an auxiliary detector (DET2) for providing an indicator signal (S2) indicative of elastic scattering coefficient of the sample region (REG1),
wherein said apparatus (500) is arranged to form a first output spectrum ($F1(\lambda)$) from the spectral intensity distribution ($I(\lambda)$) of a first group of Raman scattered light pulses ($LB1_R$), wherein the pulses of said first group of Raman scattered light pulses ($LB1_R$) are obtained from the sample region (REG1) when the indicator signal ($S2(t)$) indicates that an object (O1) is located in the sample region (REG1).

Example 13

The apparatus (500) of example 12, wherein the apparatus (500) is arranged to trigger the illuminating light pulses (LB0) according to the indicator signal ($S2(t)$), and wherein the apparatus (500) is arranged to form the first output spectrum ($F1(\lambda)$) from the spectral intensity distribution ($I(\lambda)$) of Raman scattered light pulses ($LB1_R$) obtained when the sample region (REG1) is illuminated by said triggered illuminating light pulses (LB0).

Example 14

The apparatus (500) of example 12, wherein the apparatus (500) is arranged to determine whether a Raman scattered light pulse ($LB1_R$) belongs to a first category or not, wherein the Raman scattered light pulse ($LB1_R$) is determined to belong to the first category only if the indicator signal (S2) exceeds a predetermined level (LIM1) when the Raman scattered light pulse ($LB1_R$) is obtained from the sample region (REG1), and wherein the apparatus (500) is arranged to form the first output spectrum ($F1(\lambda)$) from the spectral intensity distribution ($I(\lambda)$) of Raman scattered light pulses ($LB1_R$) of the first category.

For the person skilled in the art, it will be clear that modifications and variations of the devices and the methods according to the present invention are perceivable. The figures are schematic. The particular embodiments described above with reference to the accompanying drawings are illustrative only and not meant to limit the scope of the invention, which is defined by the appended claims.

The invention claimed is:

1. A method for measuring Raman scattering, the method comprising:
   varying composition in a sample region,
   providing an indicator signal indicative of elastic scattering coefficient of the sample region,
   illuminating the sample region with illuminating light pulses,
   forming a first output spectrum from the spectral intensity distribution of a first group of Raman scattered light pulses, wherein the pulses of said first group of Raman scattered light pulses are obtained from the sample region when the indicator signal indicates that an object is located in the sample region,
   determining whether a Raman scattered light pulse belongs to a first category or not, wherein the Raman scattered light pulse is determined to belong to the first category only if the indicator signal exceeds a predetermined level when the Raman scattered light pulse is obtained from the sample region, and
   forming the first output spectrum from the spectral intensity distribution of Raman scattered light pulses of the first category.

2. The method of claim 1, wherein the spectral intensity distribution of the Raman scattered light pulses is measured by a detector, and the method comprises controlling operation of the detector based on the indicator signal.

3. The method of claim 1, wherein the spectral intensity distribution of the Raman scattered light pulses is measured by a detector, and the method comprises enabling operation of the detector based on the indicator signal.

4. The method of claim 1, wherein the spectral intensity distribution of the Raman scattered light pulses is measured by using an array of single photon avalanche photodiodes and a set of counters arranged to count pulses provide by the photodiodes, wherein operation of said set of counters is enabled based on the indicator signal.

5. The method of claim 1, wherein the composition is varied by moving a heterogeneous substance with respect to the sample region, and the heterogeneous substance comprises a plurality of objects suspended in a carrier medium.

6. The method of claim 1 comprising estimating a volume fraction of objects based on the indicator signal.

7. The method of claim 1, wherein the illuminating light pulses are focused to the sample region through a first lens, and the Raman scattered light from the sample region is gathered through said first lens.

8. A method for measuring Raman scattering, the method comprising:
   varying composition in a sample region,
   providing an indicator signal indicative of elastic scattering coefficient of the sample region,
   illuminating the sample region with illuminating light pulses,
   forming a first output spectrum from the spectral intensity distribution of a first group of Raman scattered light pulses, wherein the pulses of said first group of Raman scattered light pulses are obtained from the sample region when the indicator signal indicates that an object is located in the sample region,
   determining whether a Raman scattered light pulse belongs to a first category or to a second category based on the indicator signal, wherein the Raman scattered light pulse is determined to belong to the first category if the indicator signal exceeds a predetermined level when the Raman scattered light pulse is obtained from the sample region, and wherein the Raman scattered light pulse is determined to belong to the second category if the indicator signal is lower than said predetermined level when the Raman scattered light pulse is obtained from the sample region,
   forming the first output spectrum from the spectral intensity distribution of Raman scattered light pulses of the first category, and
   forming a second output spectrum from the spectral intensity distribution of Raman scattered light pulses of the second category.

9. The method of claim 8, wherein the spectral intensity distribution of the Raman scattered light pulses is measured by a detector, and the method comprises controlling operation of the detector based on the indicator signal.

10. The method of claim 8, wherein the spectral intensity distribution of the Raman scattered light pulses is measured by a detector, and the method comprises enabling operation of the detector based on the indicator signal.

11. The method of claim 8, wherein the spectral intensity distribution of the Raman scattered light pulses is measured by using an array of single photon avalanche photodiodes and a set of counters arranged to count pulses provide by the photodiodes, wherein operation of said set of counters is enabled based on the indicator signal.

12. The method of claim 8, wherein the composition is varied by moving a heterogeneous substance with respect to the sample region, and the heterogeneous substance comprises a plurality of objects suspended in a carrier medium.

13. The method of claim 8 comprising estimating a volume fraction of objects based on the indicator signal.

14. The method of claim 8, wherein the illuminating light pulses are focused to the sample region through a first lens, and the Raman scattered light from the sample region is gathered through said first lens.

* * * * *